US011241427B2

(12) United States Patent
Koos et al.

(10) Patent No.: US 11,241,427 B2
(45) Date of Patent: Feb. 8, 2022

(54) SMALL MOLECULE MODULATORS OF NR2F6 ACTIVITY

(71) Applicant: Regen Biopharma, Inc., La Mesa, CA (US)

(72) Inventors: David Koos, La Mesa, CA (US); Thomas Ichim, San Diego, CA (US)

(73) Assignee: KCL Therapeutics, Inc., La Mesa, CA (US)

( * ) Notice: Subject to any disclaimer, the term of this patent is extended or adjusted under 35 U.S.C. 154(b) by 0 days.

(21) Appl. No.: 15/364,111

(22) Filed: Nov. 29, 2016

(65) Prior Publication Data
US 2019/0358224 A1    Nov. 28, 2019

Related U.S. Application Data

(60) Provisional application No. 62/260,617, filed on Nov. 29, 2015.

(51) Int. Cl.
| | |
|---|---|
| *A61K 31/496* | (2006.01) |
| *A61K 31/403* | (2006.01) |
| *A61K 31/40* | (2006.01) |
| *A61K 31/197* | (2006.01) |
| *A61K 31/164* | (2006.01) |

(52) U.S. Cl.
CPC .......... *A61K 31/496* (2013.01); *A61K 31/164* (2013.01); *A61K 31/197* (2013.01); *A61K 31/40* (2013.01); *A61K 31/403* (2013.01)

(58) Field of Classification Search
CPC .................................................. A61K 31/496
See application file for complete search history.

(56) References Cited

U.S. PATENT DOCUMENTS

| | | | | |
|---|---|---|---|---|
| 5,464,870 A | * | 11/1995 | Veronesi | A61K 31/167 514/617 |
| 2007/0072800 A1 | * | 3/2007 | Gengrinovitch | A61P 35/02 514/120 |

OTHER PUBLICATIONS

Yin et al. CAS: 168:144589, 2015.*
Shichiri et al. CAS: 154: 279, 2010.*
Safe et al. Mol Endocrinol., 2014, 28(2):157-72 (abstract).*

* cited by examiner

*Primary Examiner* — Rei Tsang Shiao
(74) *Attorney, Agent, or Firm* — Baumgartner Patent Law; Marc Baumgartner

(57) ABSTRACT

Disclosed are compounds useful for alteration of NR2F6 activity. In some embodiments of the invention compounds disclosed are utilized for stimulation of NR2F6 activity, alone, or in combination with PKC activation. In other embodiments, the invention teaches use of compounds for inhibition of NR2F6 activation. Stimulation of NR2F6 within the context of the invention is useful, intra alia, for induction of immune inhibition, or stimulation of cellular proliferation without significant induction of differentiation. Inhibition of NR2F6 is desired in situations where the practitioner of the invention seeks to augment immune response, or induce cellular differentiation. In another embodiment, inhibition of NR2F6 expression is desired in situations where inhibition of cancer or cancer stem cells is needed.

9 Claims, No Drawings

Specification includes a Sequence Listing.

SMALL MOLECULE MODULATORS OF NR2F6 ACTIVITY

CROSS-REFERENCE TO RELATED APPLICATIONS

The present invention claims priority to provisional U.S. patent application No. 62/260,617, filed Nov. 29, 2015, which is hereby incorporated in its entirety including all tables, figures, and claims.

SEQUENCE LIST

The instant application contains a Sequence Listing which has been filed electronically in ASCII format and is hereby incorporated by reference in its entirety. Said ASCII copy, created on Dec. 17, 2018, is named Regen-SmallMoleculeNP1_SL.txt and is 6,275 bytes in size.

FIELD OF THE INVENTION

The invention pertains to modulators of nuclear receptor activity, more specifically, the invention relates to modulation of NR2F6 utilizing compounds, more specifically the invention pertains to immune modulation and modulation of cancer stem cell activity through administration of compounds described herein.

BACKGROUND

Understanding the mechanisms of immune modulation will lead to development of new cancer treatments. The immune system is comprised of activatory and inhibitory mechanisms which allow for tight control of immune responses and subsequent inhibition of responses after clearance of the immune target. At a very basic level, one may consider that the central event stimulating immune responses is the antigen-specific activation of naive $CD4^+$ T cells subsequent to binding antigen presenting cell MHC containing antigenic peptide [1, 2]. The CD4+ T cell, also known as the "helper T cell" coordinates the activation of the adaptive immune response, being critical for stimulation of cytotoxic CD8+ T cells, whose role is to destroy host cells affected by cancer, viruses, and intracellular bacteria, as well as to stimulate B cell maturation to eventual plasma cell differentiation, which is responsible for antibody production. Antibodies being critical molecules in clearance of extracellular pathogens such as various bacteria and parasites. It is generally accepted that, under most circumstances, naive CD4+ T cells require two distinct signals to proliferate and differentiate into the armed effector cells that mediate adaptive immunity [3]. Signal 1 of this two-signal model is antigen-specific and is generated by interaction of the TCR with antigenic peptide presented in context with MHC II antigens. This results in transduction of TCR intracellular signals leading to production of IL-2 and T cell activation. Signal 2 is referred to as a costimulatory signal because, while essential, it does not by itself induce any functional response in T cells. The best characterized costimulatory signal 2 is generated through the T cell surface molecule CD28 [4, 5]. CD28 delivers a costimulatory signal upon interaction with CD80 and/or CD86) present on B cells, macrophage, or dendritic cells [6]. Activation of the TCR in the presence of costimulatory signals leads to T cell clonal expansion and initiation of effector functions such as IL-2 production.

In the situation of cancer, immune inhibitory mechanisms, termed immune checkpoints, are prematurely activated in order for the tumor to escape immune attack. Two main immune checkpoints exist: a) CTLA-4, which sends an inhibitory signal to T cells upon binding CD80 and/or CD86 on antigen presenting cells [7-9], and; b) PD-1, which binds to PD-1 ligand on tumor cells, stromal cells, or antigen presenting cells [10, 11].

CTLA-4 is related to CD28, however instead of activating T cells in a co-stimulatory manner, it leads to inhibition or co-inhibition of T cells [12]. In the current invention we disclose means of using small molecule compounds as immune modulators.

DESCRIPTION OF THE INVENTION

For the purposes of advancing and clarifying the principles of the invention disclosed herein, reference will be made to certain embodiments and specific language will be used to describe said embodiments. It will nevertheless be understood and made clear that no limitation of the scope of the invention is thereby intended. The alterations, further modifications and applications of the principles of the invention as described herein serve only as specific embodiment, however one skilled in the art to which the invention relates will understand that the following are indeed only specific embodiments for illustrative purposes, and will derive similar types of applications upon reading and understanding this disclosure. To allow for the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The invention provides means of modulating the immune system using compounds that alter activity of NR2F6, otherwise known as nuclear orphan receptor Ear2. NR2F6 belongs to the nuclear receptor (NR) superfamily of ligand-activated receptors, which exhibit a common modular structure and are involved in various homeostatic functions, but also play a critical role in oncogenesis and cancer propagation [13]. Specifically, studies have shown that members of the NR family regulate development, reproduction, and metabolism of lipids, drugs and energy. The importance of this family of proteins in metabolic disease is exemplified by NR ligands used in the clinic or under exploratory development for the treatment of diabetes mellitus, dyslipidemia, hypercholesterolemia, or other metabolic abnormalities. Genetic studies in humans and rodents support the notion that NRs control a wide variety of metabolic processes by regulating the expression of genes encoding key enzymes, transporters and other proteins involved in metabolic homeostasis [14-16]. Genomic sequence availability has led to the identification of 48 NRs encoded by the human genome and 49 NRs encoded by the mouse genome [15, 17].

The complex interplay between the activation or deactivation of NRs by different structural classes of endogenous and endogenous ligands, such as the steroid and thyroid hormones, lipids, vitamins and other biochemicals, is essential for their function. The 48 NR family members are classified into subgroups based on the identification of endogenous ligands for each receptor. The endocrine receptors include the steroid hormone receptors that bind steroid hormones and the heterodimeric receptors that partner with the retinoid X receptor and bind thyroid hormones, retinoids, and vitamin D. The identification of specific endogenous ligands for the endocrine receptors has facilitated the design and development of selective receptor modulators (SRMs) that exhibit tissue-specific agonist or antagonist activities [18-23] and are used extensively for treatment of hormone-/hormone receptor-dependent diseases [24, 25]. Tamoxifen is one of many selective estrogen receptor (ER) modulators used in endocrine therapies for treating ER-positive breast cancer patients [26, 27].

Adopted orphan receptors are a subtype of NRs that are subdivided into groups based on their ligands. The lipid sensor receptor subtypes and their ligands include retinoid X receptor (9-cis-retinoic acid) [28-31], peroxisome proliferator-activated receptors (PPARs) (fatty acids) [32, 33], liver X receptor (oxysterols), farnesoid X receptor (bile acids), and pregnane X receptor [34], which binds cholesterol derivatives. Retinoid X receptors have been found in various cancer stem cells and methodologies for their utilization, as well as ligands/synthetic ligands targeting them are provided in the following references, which can be utilized by one of skill in the art to practice the current invention which provides compounds useful for modulating the NR2F6 nuclear receptor [35-51]. Means of modulating PPARs are also amenable to utilization in the context of the current invention, references are provided, whose methodology may be adapted for use with the compounds presented in the current invention for treatment of cancer or immune modulation [52-63]. With regard to PPARs, three known subtypes of the PPAR family are PPARα, PPARγ, and PPARδ. The PPARγ is abundantly expressed in many cell types, where it regulates lipid metabolism, glucose homeostasis, tumour progression, and inflammation. Polyunsaturated fatty acids, eicosanoids, prostaglandins, and linoleic acid have been identified as endogenous ligands for PPARγ, whereas thiazolidinedione class of compounds function as high-affinity synthetic agonists for PPARγ subsequent to exposure to with specific ligands, PPARγ forms a heterodimer complex with retinoid X receptor, which then mediates the target gene expression. In terms of immune modulation, references are provided that can be adapted to the practice of the current invention by substituting NR2F6 specific compounds with those described for PPAR [64-83].

The enigmatic orphan receptor subtype includes constitutive androstane receptor (androstane and many drugs/xenobiotics) [84-95], hepatocyte nuclear factor-4 [96-102], and steroidogenic factor-1/liver receptor homolog 1(LRH-1) (phospholipids) [103, 104], retinoid acid-related orphan receptor (cholesterol and retinoic acids) [105-115], and estrogen-related receptor (estrogens). References provided for these receptors are herein incorporated to assist one of skill in the art in practicing the current invention which teaches the use of NR2F6 modulators for the purpose of immunotherapy.

The orphan receptors are the third class of NRs, and, as their name implies endogenous ligands for these receptors have not been identified. The crystal structure of the ligand-binding domain of the orphan receptor Nurr1 (NR4A2) shows that several hydrophobic residues protrude into the ligand-binding pocket, and a typical coactivator-binding site is lacking [116], suggesting that some orphan receptors may not bind ligands [117, 118].

Like other NR classes, the orphan receptors play important roles in cellular homeostasis and diseases including cancer, and several recent reports document the expression and potential functions of orphan receptors in different tumors and cancer cell lines. Breast tumors are routinely classified as $ER^+$ or $ER^-$, and expression of ER has prognostic significance that dictates selection of therapeutic regimens. However, analysis of $ER^+$ and $ER^-$ tumors for expression (mRNA) of all 48 NRs also demonstrated the important prognostic significance of several orphan receptors [119]. The NR4A (Nur77/TR3, Nurr1, and Nor1) and NR2F6 [v-erbA-related protein (EAR2)] receptors are uniquely overexpressed in all ($ER^+$ and $ER^-$ combined) tumors. Moreover, Nur77, EAR2, and chicken ovalbumin upstream promoter transcription factor II (COUP-TFII) are among a limited group of NRs that are prognostic for breast cancer classification and histologic grade, and COUP-TFII expression was a positive prognostic factor for tamoxifen-treated $ER^+$ breast cancer patients [119]. Examination of lung tumor and nontumor tissue indicated highly variable NR expression; however, gene combinations and individual receptors, such as the orphan receptor small heterodimer partner (SHP, NR0B2), predicted enhanced survival for early-stage lung cancer patients [120]. Moreover, expression of Nur77 in normal lung epithelium from patients was an indicator for good prognosis [121]. NR profiling of the NCI60 cancer cell panel demonstrated that relative expression levels of some orphan receptors also correlated with drug sensitivity [122]. For example, cancer cell sensitivity to microtubule-disrupting drugs was enhanced in cells expressing low levels of NR2F6 and COUP-TFII, whereas high levels of the orphan receptor tailless (TLX, NR2E1) correlated with sensitivity to 9-fluoroprednisolone [122].

In the context of the present invention, the term "NR2F6" relates to "nuclear receptor subfamily 2, group F, member 6" or "Ear2" as described in the art. Nuclear receptors are transcription factors that regulate the expression of specific target genes, thereby orchestrating a wide array of cellular processes including cellular activation, development and disease progression. The nuclear receptor super-family consists of receptors that bind to hormones and orphan receptors with yet undefined endogenous ligands. The COUP-TF orphan receptors are known to be preferentially expressed in the central nervous system and organs that depend on the interaction between mesenchyme and epithelial layers. The three mammalian COUP-TF family members are NR2F1/Ear3, NR2F2/Arp1 and NR2F6. The established target genes of said COUP-TF family members are apolipoproteins and retinoic acid-, peroxisome-, oxytocin-, estrogen- and vitamin D receptors. By yeast 1-hybrid screen and in vitro assays with recombinant NR2F6 it was found that the TGACCT direct-repeat motif is the DNA binding sequence of NR2F6 and that overexpression of NR2F6 induces repression of the renin gene transcription in a DNA-binding-specific manner [123]. Wild type human NR2F6 is known to possess the following nucleotide sequence, SEQ ID No. 1: gtgcagcccg tgccccccgc gcgccggggc cgaatgcgcg ccgcgtaggg tcccccgggc 61 cgagagggggt gcccggaggg aagagcgcgg tggggcgcc ccggccccgc tgccctgggg 121 ctatggccat ggtgaccggc ggctggggcg gccccggcgg cgacacgaac ggcgtggaca 181 aggcgggcgg ctacccgcgc gcggccgagg acgactcggc ctcgccccc ggtgccgcca 241 gcgacgccga gccgggcgac gaggagcggc cggggctgca ggtggactgc gtggtgtgcg 301 gggacaagtc gagcggcaag cattacggtg tcttcacctg cgagggctgc aagagcttt 361 tcaagcgaag catccgccgc aacctcagct acacctgccg gtccaaccgt gactgccaga 421 tcgaccagca ccaccggaac cagtgccagt actgccgtct caagaagtgc ttccgggtgg 481 gcatgaggaa ggaggcggtg cagcgcggcc gcatcccgca ctcgctgcct ggtgccgtgg 541 ccgcctcctc gggcagcccc ccgggctcgg cgctggcggc agtggcgagc ggcggagacc 601 tcttcccggg gcagccggtg tccgaactga tcgcgcagct gctgcgcgct gagccctacc 661 ctgcggcggc cggacgcttc ggcgcagggg gcggcgcggc gggcgcggtg ctgggcatcg 721 acaacgtgtg cgagctggcg gcgcggctgc tcttcagcac cgtggagtgg gcgcgccacg 781 cgcccttctt ccccgagctg ccggtggccg accaggtggc gctgctgcgc ctgagctgga 841 gcgagctctt cgtgctgaac gcggcgcagg cggcgctgcc cctgcacacg gcgccgctac 901 tggccgccgc cggcctccac gccgcgccta tggccgccga gcgcgccgtg gctttcatgg 961 accaggtgcg cgccttccag gaggaggtgg acaagctggg ccgcctgcag gtcgactcgg 1021 ccgagtatgg ctgcctcaag gccatcgcgc tcttcacgcc cgacgcctgt ggcctctcag 1081 acccggccca cgttgagagc ctgcaggaga aggcgcaggt ggccctcacc gagtatgtgc 1141 gggcgcagta cccgtcccag ccccagcgct tcgggcgcct gctgctgcgg ctccccgccc 1201 tgcgcgcggt ccctgcctcc ctcatctccc agctgttctt catgcgcctg gtggggaaga 1261 cgcccattga gacactgatc agagacatgc tgctgtcggg gagtaccttc aactggccct 1321 acggctcggg ccagtgacca tgacggggcc acgtgtgctg tggccaggcc tgcagacaga 1381 cctcaaggga cagggaatgc tgaggcctcg aggggcctcc cggggcccag gactctggct 1441 tctctcctca gacttctatt ttttaaagac tgtgaaatgt ttgtcttttc tgtttttttaa 1501 atgatcatga aaccaaaaag agactgatca tccaggcctc agcctcatcc tccccaggac 1561 ccctgtccag gatggagggt ccaatcctag gacagccttg ttcctcagca ccctagcat 1621 gaacttgtgg gatggtgggg ttggcttccc tggcatgatg gacaaaggcc tggcgtcggc 1681 cagagggggct gctccagtgg gcaggggtag ctagcgtgtg ccaggcagat cctctggaca 1741 cgtaacctat gtcagacact acatgatgac tcaaggccaa taataaagac atttcctacc 1801 tgca, which corresponds to the following amino acid sequence, SEQ ID NO: 2:

MAMVTGGWGGPGGDTNGVDKAGGYPRAAEDDSASPPGAASDAEPGD

EERPGLQVDCVVCGDKSSGKHYGVFTCEGCKSFFKRSIRRNLSYTC

RSNRDCQIDQHHRNQCQYCRLKKCFRVGMRKEAVQRGRIPHSLPGA

VAASSGSPPGSALAAVASGGDLFPGQPVSELIAQLLRAEPYPAAAG

RFGAGGGAAGAVLGIDNVCELAARLLFSTVEWARHAPFFPELPVAD

QVALLRLSWSELFVLNAAQAALPLHTAPLLAAAGLHAAPMAAERAV

AFMDQVRAFQEQVDKLGRLQVDSAEYGCLKAIALFTPDACGLSDPA

HVESLQEKAQVALTEYVRAQYPSQPQRFGRLLLRLPALRAVPASLI

SQLFFMRLVGKTPIETLIRDMLLSGSTFNWPYGSGQ.

Accordingly, the invention discloses compounds that bind to NR2F6 molecules or to portion of NR2F6, which as are at least 60%, 70%, 80%, 90%, 95%, 96%, 97%, 98% or 99% identical to the amino acid sequence of NR2F6. The term "agonist" or "activator" as used herein is known in the art and relates to a compound/substance capable of fully or partially stimulating the physiologic activity of (a) specific receptor(s). In the context of the present invention said agonist, therefore, may stimulate the physiological activity of a receptor such as NR2F6 upon binding of said compound/substance to said receptor. Binding of an "agonist/activator" to a given receptor, e.g. NR2F6, may mimic the action of an endogenous ligand binding to said receptor. As used herein, accordingly, the term "agonist" also encompasses partial agonists or co-agonists/co-activators. In addition thereto, however, an "agonist" or "activator" of NR2F6 in the context of the present invention may also be capable of stimulating the function of a given receptor, such as NR2F6, by inducing/enhancing the expression of the nucleic acid molecule encoding for said receptor. Thus, an agonist/activator of NR2F6 may lead to an increased expression level of NR2F6 (e.g. increased level of NR2F6 mRNA, NR2F6 protein) which is reflected in an increased activity of NR2F6. This increased activity can be measured/detected by the herein described methods. An activator of NR2F6 in the context of the present invention, accordingly, may also encompass transcriptional activators of NR2F6 expression that are capable of enhancing NR2F6 function. The term "agonist" comprises partial agonists. As partial agonists the art defines candidate molecules that behave like agonists, but that, even at high concentrations, cannot activate NR2F6 to the same extend as a full agonist. As described herein below in detail, the increased expression and/or activity of NR2F6 by an agonist/activator of NR2F6 leads to a decreased activity (and/or expression) of components of the NR2F6-dependent signaling pathway; in particular the activity of NF-AT and AP-1 is decreased. NF-AT/AP-1 regulate transcription/expression of further "downstream" components of the NR2F6-dependent signaling pathway, such as IL-2, IL-17 and/or IFN-gamma. A decrease in NF-AT/AP-1 activity results in a decreased transcription of these "downstream" components (e.g. IL-2, IL-17 and/or IFN-gamma) which in turn leads to a suppression of an immune response. In sum, the herein described agonist/activator of NR2F6 will, accordingly, lead to a suppression of an immune response. Hence, the use of potent agonists/activators of NR2F6 will lead to a higher expression and/or activity of NR2F6. In accordance with the above definition of "agonist" or "activator" also NR2F6 itself can be considered as its own agonist/activator. For example, overexpression of NR2F6 may lead to enhanced NR2F6 activity, thus agonizing NR2F6 function. Accordingly, NR2F6 as defined herein can be used for the treatment of a disease related to an augmented immune response. For example, NR2F6 may be used in accordance with the present invention, wherein NR2F6 is (a) a polypeptide comprising an amino acid encoded by a nucleic acid molecule having the nucleic acid sequence of NR2F6; (b) a polypeptide having an amino acid sequence of NR2F6 (c) a polypeptide encoded by a nucleic acid molecule encoding a peptide having an NR2F6 amino acid sequence; (d) a polypeptide comprising an amino acid encoded by a nucleic acid molecule hybridizing under stringent conditions to the complementary strand of nucleic acid molecules as defined in (a) or (c) and encoding a NR2F6 or a functional fragment thereof; (e) a polypeptide having at least 60% homology to the polypeptide of any one of (a) to (d), whereby said polypeptide is a NR2F6 or a functional fragment thereof; or (f) a polypeptide comprising an amino acid encoded by a nucleic acid molecule being degenerate as a result of the genetic code to the nucleotide sequence of a nucleic acid molecule as defined in (a), (c) and (d). As described herein below in more detail, the increase of NR2F6 activity leads to a decreased activity of NF-AT/AP-1 (and other components of the NR2F6-dependent signalling pathway) which in turn results in a suppressed immune response. An exemplary transfection of CD4.sup.+ T cells with a construct for the overexpression of NR2F6 is also shown in the appended examples. As demonstrated therein, overexpression (about 5-fold increase over normal expression level) leads to a diminished IL-2 activity/expression and consequently to a reduced IL-2 amount, resulting in a reduced immune response. Therefore, it is clear that agonists/activators of NR2F6 are useful in the treatment of diseases where suppression of the immune response is desired (e.g. diseases with an overstimulated immune response, such as allergies and multiple sclerosis). As used herein the term "overexpression" means that the NR2F6 activity/expression is at least 1-fold, 2-fold, 3-fold, 4-fold, 5-fold, 6-fold, 7-fold, 8-fold, 9-fold, preferably at least 10-fold, or more preferably at least 25-fold increased in comparison to a (control) standard value as defined herein, wherein a 25 fold expression level over normal can be considered as a maximum overexpression level.

The terms "immune response" or "immune reaction" as used herein are known in the art and relate to the response/reaction of the immune system to an antigen. In case of an "immune response", accordingly, immune cells are activated in such way that (a) specific function(s) of said immune cells is/are induced. Said "immune cells" may include, but are not limited to, B cells, T cells, neutrophils, eosinophils, basophils, mast cells, macrophages and dendritic cells. Said "(a) specific function(s) of activated immune cells" may include, but are not limited to, secretion of antibodies, presentation of antigen, proliferation of said immune cells, secretion of cytokines such as interleukin-2 (IL-2), interleukin-17 (IL-17) or interferon gamma (IFNgamma), expression of regulatory-, activation- and/or adhesion molecules, and the ability to induce apoptosis and/or cytolysis. The term "antigen" as used herein refers to any substance capable of inducing an immune response. It is of note that an antigen typically is associated with a foreign substance (i.e. a "non-self antigen"). In addition thereto, however, an own body-derived substance (i.e. a "self antigen") may also induce an immune response. As used herein, accordingly, the term "immune response" also encompasses "auto-immune responses" or "auto-immune reactions".

"Treating a cancer", "inhibiting cancer", "reducing cancer growth" refers to inhibiting or preventing oncogenic activity of cancer cells. Oncogenic activity can comprise inhibiting migration, invasion, drug resistance, cell survival, anchorage-independent growth, non-responsiveness to cell death signals, angiogenesis, or combinations thereof of the cancer cells. The terms "cancer", "cancer cell", "tumor", and "tumor cell" are used interchangeably herein and refer generally to a group of diseases characterized by uncontrolled, abnormal growth of cells (e.g., a neoplasia). In some forms of cancer, the cancer cells can spread locally or through the bloodstream and lymphatic system to other parts of the body ("metastatic cancer"). "Ex vivo activated lymphocytes", "lymphocytes with enhanced antitumor activity" and "dendritic cell cytokine induced killers" are terms used interchangeably to refer to composition of cells that have been activated ex vivo and subsequently reintroduced within the context of the current invention. Although the word "lymphocyte" is used, this also includes heterogenous cells that have been expanded during the ex vivo culturing process including dendritic cells, NKT cells, gamma delta T cells, and various other innate and adaptive immune cells. As used herein, "cancer" refers to all types of cancer or neoplasm or malignant tumors found in animals, including leukemias, carcinomas and sarcomas. Examples of cancers are cancer of the brain, melanoma, bladder, breast, cervix, colon, head and neck, kidney, lung, non-small cell lung, mesothelioma, ovary, prostate, sarcoma, stomach, uterus and Medulloblastoma. The term "leukemia" is meant broadly progressive, malignant diseases of the hematopoietic organs/systems and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, and promyelocytic leukemi.

The term "carcinoma" refers to a malignant new growth made up of epithelial cells tending to infiltrate the surrounding tissues, and/or resist physiological and non-physiological cell death signals and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrmcous carcinoma, carcinoma villo sum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, and carcinoma scroti, The term "sarcoma" generally refers to a tumor which is made up of a substance like the embryonic connective tissue and is generally composed of closely packed cells embedded in a fibrillar, heterogeneous, or homogeneous substance. Sarcomas include, chondro sarcoma, fibro sarcoma, lympho sarcoma, melano sarcoma, myxo sarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma. Additional exemplary neoplasias include, for example, Hodgkin's Disease, Non-Hodgkin's Lymphoma, multiple myeloma, neuroblastoma, breast cancer, ovarian cancer, lung cancer, rhabdomyo sarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer.

In some particular embodiments of the invention, the cancer treated is a melanoma. The term "melanoma" is taken to mean a tumor arising from the melanocytic system of the skin and other organs. Melanomas include, for example, Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma. The term "polypeptide" is used interchangeably with "peptide", "altered peptide ligand", and "flourocarbonated peptides." The term "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

The term "T cell" is also referred to as T lymphocyte, and means a cell derived from thymus among lymphocytes involved in an immune response. The T cell includes any of a CD8-positive T cell (cytotoxic T cell: CTL), a CD4-positive T cell (helper T cell), a suppressor T cell, a regulatory T cell such as a controlling T cell, an effector cell, a naive T cell, a memory T cell, an .alpha..beta.T cell expressing TCR .alpha. and .beta. chains, and a .gamma..delta.T cell expressing TCR .gamma. and .delta. chains. The T cell includes a precursor cell of a T cell in which differentiation into a T cell is directed. Examples of "cell populations containing T cells" include, in addition to body fluids such as blood (peripheral blood, umbilical blood etc.) and bone marrow fluids, cell populations containing peripheral blood mononuclear cells (PBMC), hematopoietic cells, hematopoietic stem cells, umbilical blood mononuclear cells etc., which have been collected, isolated, purified or induced from the body fluids. Further, a variety of cell populations containing T cells and derived from hematopoietic cells can be used in the present invention. These cells may have been activated by cytokine such as IL-2 in vivo or ex vivo. As these cells, any of cells collected from a living body, or cells obtained via ex vivo culture, for example, a T cell population obtained by the method of the present invention as it is, or obtained by freeze preservation, can be used. The term "antibody" is meant to include both intact molecules as well as fragments thereof that include the antigen-binding site. Whole antibody structure is often given as H.sub.2L.sub.2 and refers to the fact that antibodies commonly comprise 2 light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity. The variable regions of either H or L chains contains the amino acid sequences capable of specifically binding to antigenic targets. Within these sequences are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure. The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have 3 CDR regions, each non-contiguous with the others (termed L1, L2, L3, H1, H2, H3) for the respective light (L) and heavy (H) chains. The antibodies disclosed according to the invention may also be wholly synthetic, wherein the polypeptide chains of the antibodies are synthesized and, possibly, optimized for binding to the polypeptides disclosed herein as being receptors. Such antibodies may be chimeric or humanized antibodies and may be fully tetrameric in structure, or may be dimeric and comprise only a single heavy and a single light chain.

The term "effective amount" or "therapeutically effective amount" means a dosage sufficient to treat, inhibit, or alleviate one or more symptoms of a disease state being treated or to otherwise provide a desired pharmacologic and/or physiologic effect, especially enhancing T cell response to a selected antigen. The precise dosage will vary according to a variety of factors such as subject-dependent variables (e.g., age, immune system health, etc.), the disease, and the treatment being administered.

The terms "individual", "host", "subject", and "patient" are used interchangeably herein, and refer to a mammal, including, but not limited to, primates, for example, human beings, as well as rodents, such as mice and rats, and other laboratory animals.

As used herein, the term "treatment regimen" refers to a treatment of a disease or a method for achieving a desired physiological change, such as increased or decreased response of the immune system to an antigen or immunogen, such as an increase or decrease in the number or activity of one or more cells, or cell types, that are involved in such response, wherein said treatment or method comprises administering to an animal, such as a mammal, especially a human being, a sufficient amount of two or more chemical agents or components of said regimen to effectively treat a disease or to produce said physiological change, wherein said chemical agents or components are administered together, such as part of the same composition, or administered separately and independently at the same time or at different times (i.e., administration of each agent or component is separated by a finite period of time from one or more of the agents or components) and where administration of said one or more agents or components achieves a result greater than that of any of said agents or components when administered alone or in isolation.

The term "anergy" and "unresponsiveness" includes unresponsiveness to an immune cell to stimulation, for example, stimulation by an activation receptor or cytokine. The anergy may occur due to, for example, exposure to an immune suppressor or exposure to an antigen in a high dose. Such anergy is generally antigen-specific, and continues even after completion of exposure to a tolerized antigen. For example, the anergy in a T cell and/or NK cell is characterized by failure of production of cytokine, for example, interleukin (IL)-2. The T cell anergy and/or NK cell anergy occurs in part when a first signal (signal via TCR or CD-3) is received in the absence of a second signal (costimulatory signal) upon exposure of a T cell and/or NK cell to an antigen. The term "enhanced function of a T cell", "enhanced cytotoxicity" and "augmented activity" means that the effector function of the T cell and/or NK cell is improved. The enhanced function of the T cell and/or NK cell, which does not limit the present invention, includes an improvement in the proliferation rate of the T cell and/or NK cell, an increase in the production amount of cytokine, or an improvement in cytotoxity. Further, the enhanced function of the T cell and/or NK cell includes cancellation and suppression of tolerance of the T cell and/or NK cell in the suppressed state such as the anergy (unresponsive) state, or the rest state, that is, transfer of the T cell and/or NK cell from the suppressed state into the state where the T cell and/or NK cell responds to stimulation from the outside. The term "expression" means generation of mRNA by transcription from nucleic acids such as genes, polynucleotides, and oligonucleotides, or generation of a protein or a polypeptide by transcription from mRNA. Expression may be detected by means including RT-PCR, Northern Blot, or in situ hybridization, "Suppression of expression" refers to a decrease of a transcription product or a translation product in a significant amount as compared with the case of no suppression. The suppression of expression herein shows, for example, a decrease of a transcription product or a translation product in an amount of 30% or more, preferably 50% or more, more preferably 70% or more, and further preferably 90% or more.

An "augmented immune response" is characterized by a particularly strong response/reaction of the immune system to the presence of an antigen. Under normal, non-pathological conditions, immune responses are regulated in a tightly controlled fashion. Moreover, immune responses are self-limiting and decline in time after exposure to the antigen. In case of an "augmented immune response" however, the immune response may be hypersensitive, i.e. the immune response may cause damage to the organism's own cells/tissue in presence of an antigen. Furthermore in some cases of an "augmented immune response" for example in auto-immune diseases/disorders or in transplant rejects (and the like), the immune system may fail to distinguish between self and non-self substances. The term "disease related to an augmented immune response", accordingly, relates to any disease/disorder in which an "augmented immune response" as defined herein above is etiological for, associated with, secondary to or the resultant of said disorder. An augmented immune response may be determined by directly or indirectly measuring parameters which are indicative for the magnitude of the immune response/reaction to an antigen and comparing the outcome of said measurement raised in a to be tested subject with the outcome of the same test in a physiologically normal subject. Parameters indicative for the magnitude of the immune response/reaction may include, but are not limited to the presence/quantity of (specific) antibodies, presence/quantity of (specific) immune cells, the presence/quantity of (specific) cytokines and/or the presence/quantity of (specific) regulatory-, activation- and/or adhesion molecules. For a disease to be related to an augmented immune response, accordingly, said augmented immune response may be detectable preceding, during or following said disease. In a preferred embodiment, the disease related to an augmented immune response is selected from the group consisting of acute or chronic transplant rejection, dermatological disease, T- and B-cell-mediated inflammatory disease, graft-versus-host disease and autoimmune disease. In another preferred embodiment, said dermatological disease is psoriasis, atopic dermatitis or contact allergy. In another preferred embodiment, said T- and B-cell-mediated inflammatory disease is asthma or chronic obstructive pulmonary disease (COPD). In yet another preferred embodiment, said graft-versus-host disease is acute (or fulminant) graft-versus-host disease or chronic graft-versus-host disease. In yet another preferred embodiment, said auto-immune disease is multiple sclerosis, inflammatory bowel disease, like ulcerative colitis or Behcet's disease; lupus erythematosus, pemphigus vulgaris, pemphigus foliaceus, myasthenia gravis, polymyositis, mixed collective tissue disease (MCTD) rheumatoid arthritis, diabetes mellitus, celiac disease, atherosclerosis, Goodpasture's syndrome, Grave's disease, autoimmune hepatitis/hepatic autoimmune diseases, autoimmune thrombocytopenic purpura, granulomatosis (e.g. morbus Wegener) or autoimmune haemolytic anaemia.

Immune responses are exquisitely controlled, requiring multiple finely tuned levels of activation as well as inactivation signals. In T lymphocytes among these signalling networks, T cell receptor (TCR) stimulation activates NF-AT/AP-1, a family of transcription factors that is of particular importance during immune cell activation. NF-AT mediates the transcriptional induction of "cell fate-determining genes", which govern as diverse outcomes as activation, anergy or apoptosis Mechanistically, the rise of intracellular $Ca^{2+}$ triggered by antigen binding to the TCR leads to the activation of calcineurin's phosphatase activity. This leads to dephosphorylation of phopsho-sites within the N-terminal regulatory domain on NF-AT and, subsequently, nuclear import of NF-AT. Upon transient stimuli, however, feedback inhibition, mediated via GSK3 (glycogen synthase kinase 3), CK1 (casein kinase 1) and DYRK (dual-specificity tyrosine phosphorylation-regulated kinase) protein kinases are known to counter-regulate NF-AT nuclear occupancy by rephosphorylation, which induces the nuclear export of NF-AT and the abort of immune activation-associated gene transcription. NF-AT family members are also subject to regulation in the nucleus through their ability to directly interact with other transcriptional regulatory factors. NF-AT is known to require a protein partner for high-affinity binding at most DNA sites. NF-AT complexes mostly contain cell type- or cell lineage—specific protein binding partners. In cardiac, skeletal, and smooth muscle cells, NF-AT forms complexes with GATA proteins. Accordingly, the present invention discloses agonists/activators of NR2F6 for the treatment of a disease related to an augmented immune response. Moreover, the present invention relates to the use of an agonist/activator of NR2F6 for the preparation of a medicament for the treatment of a disease related to an augmented immune response. The utilization of NR2F6 modulating compounds for alteration of immune response may be utilized by administering in patients suffering from cancer in which increased efficacy of a cancer vaccine is desired. In these situations, inhibition of NR2F6 is desired, together with immune stimulation. Accordingly in one embodiment, inhibitor compounds of NR2F6 are administered with a cancer antigen, said cancer antigens include Other antigens may be used to replace ROBO-4 and these include: a) Fos-related antigen 1; b) LCK; c) FAP; d) VEGFR2; e) NA17; f) PDGFR-beta; g) PAP; h) MAD-CT-2; i) Tie-2; j) PSA; k) protamine 2; l) legumain; m) endosialin; n) prostate stem cell antigen; o)carbonic anhydrase IX; p) STn; q) Page4; r) proteinase 3; s) GM3 ganglioside; t) tyrosinase; u) MART1; v) gp100; w) SART3; x) RGS5; y) SSX2; z) Globoll; aa) Tn; ab) CEA; ac) hCG; ad) PRAME; ae) XAGE-1; af) AKAP-4; ag) TRP-2; ah) B7H3; ai) sperm fibrous sheath protein; aj) CYP1B1; ak) HMWMAA; al) sLe (a); am) MAGE Al; an) GD2; ao) PSMA; ap) mesothelin; aq) fucosyl GM1; ar) GD3; as) sperm protein 17; at) NY-ESO-1; au) PAX5; av) AFP; aw) polysialic acid; ax) EpCAM; ay) MAGE-A3; az) mutant p53; ba) ras; bb) mutant ras; bc) NY-BR1; bd) PAX3; be) HER2/neu; bf) OY-TES1; bg) HPV E6 E7; bh) PLAC1; bi) hTERT; bj) BORIS; bk) ML-IAP; bl) idiotype of b cell lymphoma or multiple myeloma; bm) EphA2; bn) EGFRvIII; bo) cyclin B 1; bp) RhoC; bq) androgen receptor; br) surviving; bs) MYCN; bt) wildtype p53; bu) LMP2; by) ETV6-AML; bw) MUC1; bx) BCR-ABL; by) ALK; bz) WT1; ca) ERG (TMPRSS2 ETS fusion gene); cb) sarcoma translocation breakpoint; cc) STEAP; cd) OFA/iLRP; and ce) Chondroitin sulfate proteoglycan 4 (CSPG4).

Molecules provided in the current disclosure are considered "candidate molecules", which as used herein refers to a molecule or substance or compound or composition or agent or any combination thereof to be tested by one or more screening method(s) of the invention as a putative agonist or activator of NR2F6 function, activity or expression. A test compound can be any chemical, such as an inorganic chemical, an organic chemical, a protein, a peptide, a carbohydrate, a lipid, or a combination thereof or any of the compounds, compositions or agents described herein. It is to be understood that the term "candidate molecule" when used in the context of the present invention is interchangeable with the terms "test compound", "test molecule", "test substance", "potential candidate", "candidate" or the terms mentioned herein above. Potential candidate molecules or candidate mixtures of molecules to be used when contacting a cell expressing/comprising a reporter construct for NR2F6 activity as defined and described herein may be, inter alia, substances, compounds or compositions which are of chemical or biological origin, which are naturally occurring and/or which are synthetically, recombinantly and/or chemically produced. Thus, candidate molecules may be proteins, protein-fragments, peptides, amino acids and/or derivatives thereof or other compounds as defined herein, which bind to and/or interact with NR2F6, regulatory proteins/sequences of NR2F6 function or functional fragments thereof. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.) are readily producible. Additionally, natural and synthetically produced libraries and compounds are readily modified through conventional chemical, physical, and biochemical means. Results obtained from deorphanisation programs based on phylogenetic analysis methods may aid to find the natural ligand for the NR2F6 orphan receptor and, thus, will allow in silico profiling of potential ligands for NR2F6.

In the context of the present invention, libraries of compounds, particularly the compounds already identified, are screened to identify compounds that function as an agonist or activator of NR2F6. First, a library of small molecules is generated using methods of combinatorial library formation well known in the art. U.S. Pat. Nos. 5,463,564 and 5,574,656 are two such teachings. Then the library compounds are screened to identify those compounds that possess desired structural and functional properties. U.S. Pat. No. 5,684,711, discusses a method for screening libraries. To illustrate the screening process, the target cell or gene product and chemical compounds of the library are combined and permitted to interact with one another. A labelled substrate is added to the incubation. The label on the substrate is such that a detectable signal is emitted from metabolized substrate molecules. The emission of this signal permits one to measure the effect of the combinatorial library compounds on the enzymatic activity of target enzyme/activity of target protein by comparing it to the signal emitted in the absence of combinatorial library compounds. The characteristics of each library compound are encoded so that compounds demonstrating activity against the cell/enzyme/target protein can be analyzed and features common to the various compounds identified can be isolated and combined into future iterations of libraries. Once a library of compounds is screened, subsequent libraries are generated using those chemical building blocks that possess the features shown in the first round of screen to have activity against the target receptor. Using this method, subsequent iterations of candidate compounds will possess more and more of those structural and functional features required to activate the target receptor, until a group of agonists/activators with high specificity for the receptor can be found. These compounds can then be further tested for their safety and efficacy as an immunosuppressant for use in animals, such as mammals. It will be readily appreciated that this particular screening methodology is exemplary only. Other methods are well known to those skilled in the art. For example, a wide variety of screening techniques are known for a large number of naturally-occurring targets when the biochemical function of the target protein is known. For example, some techniques involve the generation and use of small peptides to probe and analyze target proteins both biochemically and genetically in order to identify and develop drug leads. Such techniques include the methods described in WO 99/35494, WO 98/19162, WO 99/54728.

In one embodiment, the assessment of compounds for NR2F6 modulating activity is performed utilizing means known in the art, such as described in U.S. Pat. No. 9,091,696. Compounds useful for the screening and modification for enhanced NR2F6 modulatory activity include: CAR Agonists such as 5β-Dihydroprogesterone, 6,7-Dimethylesculetin, Amiodarone, Artemisinin, Benfuracarb, Carbamazepine, Carvedilol, Chlorpromazine, Chrysin, CITCO, Clotrimazole, Cyclophosphamide, Cypermethrin, DHEA, Efavirenz, Ellagic acid, Griseofulvin, Methoxychlor, Mifepristone, Nefazodone, Nevirapine, Nicardipine, Octicizer, Permethrin, Phenobarbital, Phenytoin, Reserpine, TCPOBOP, Telmisartan, Tolnaftate, Troglitazone, Valproic acid. CAR Antagonists such as 3,17β-Estradiol, 3α-Androstanol, 3α-Androstenol, 3β-Androstanol, 17-Androstanol, AITC, Ethinyl estradiol, Meclizine, Nigramide J, Okadaic acid, PK-11195, S-07662, T-0901317. FXR Agonists such as Bile acids, Cafestol, Chenodeoxycholic acid, Fexaramine, GW-4064, Obeticholic acid. FXR Antagonists such as Guggulsterone. LXR Agonists such as 22R-Hydroxychole sterol, 24S-Hydroxychole sterol, 27-Hydroxychole sterol, Cholestenoic acid, DMHCA, GW-3965, Hypocholamide, T-0901317. PPAR-alpha Agonists such as 15-HETE, 15-HpETE, Aleglitazar, Aluminium clofibrate, Arachidonic acid, Bezafibrate, Clofibrate, CP-775146, DHEA, Elafibranor, Fenofibrate, Gemfibrozil, GW-7647, Leukotriene B4, LG-101506, LG-100754, Lobeglitazone, Muraglitazar, Oleylethanolamide, Palmitoylethanolamide, Pemafibrate, Perfluorononanoic acid, Perfluorooctanoic acid, Pioglitazone, Saroglitazar, Sodelglitazar, Tesaglitazar, Tetradecylthioacetic acid, Troglitazone, WY-14643. PPAR-alpha Antagonists such as GW-6471, MK-886. PPAR-delta Agonists such as 15-HETE, 15-HpETE, Arachidonic acid, Bezafibrate, Elafibranor, GW-0742, GW-501516, L-165, 041, LG-101506, MBX-8025, Sodelglitazar, Tetradecylthioacetic acid. PPAR-delta Antagonists such as FH-535, GSK-0660, GSK-3787. PPAR gamma agonists such as 5-Oxo-ETE, 5-Oxo-15-hydroxy-ETE, 15-Deoxy-Δ12,14-prostaglandin J2, 15-HETE, 15-HpETE, Aleglitazar, Arachidonic acid, Berberine, Bezafibrate, Ciglitazone, Darglitazone, Edaglitazone, Etalocib, GW-1929, Ibuprofen, LG-100268, LG-100754, LG-101506, Lobeglitazone, Muraglitazar, nTZDpa, Perfluorononanoic, acid, Pioglitazone, Prostaglandin J2, Rosiglitazone, RS5444, Saroglitazar, Sodelglitazar, Telmisartan, Tesaglitazar, Troglitazone. SSPARMS such as BADGE, EPI-001, INT-131, MK-0533, S26948. PPAR gamma antagonists such as FH-535, GW-9662, SR-202, T-0070907. PPAR nonselective agonists such as Ciprofibrate, Clinofibrate, Clofibride, Englitazone, Etofibrate, Farglitazar, Netoglitazone, Ronifibrate, Rivoglitazone, Simfibrate. PXR Agonists such as 5α-Dihydroprogesterone, 5β-Dihydroprogesterone, 17α-Hydroxypregnenolone, 17α-Hydroxyprogesterone, Δ4-Androstenedione, Δ5-Androstenediol, Δ5-Androstenedione, AA-861, Allopregnanolone, Alpha-Lipoic acid, Ambrisentan, AMI-193, Amlodipine besylate, Antimycotics, Artemisinin, Aurothioglucose, Bile acids, Bithionol, Bosentan, Bumecaine, Cafestol, Cephaloridine, Cephradine, Chlorpromazine, Ciglitazone, Clindamycin, Clofenvinfos, Chloroxine, Clotrimazole, Colforsin, Corticosterone, Cyclophosphamide, Cyproterone acetate, Demecolcine, Dexamethasone, DHEA, DHEA-S, Dibunate sodium, Diclazuril, Dicloxacillin, Dimercaprol, Dinaline, Docetaxel, Docusate calcium, Dodecylbenzenesulfonic acid, Dronabinol, Droxidopa, Eburnamonine, Ecopipam, Enzacamene, Epothilone B, Erythromycin, Famprofazone, Febantel, Felodipine, Fenbendazole, Fentanyl, Flucloxacillin, Fluorometholone, Griseofulvin, Haloprogin, Hetacillin potassium, Hyperforin (Hypericum perforatum), Indinavir sulfate, Lasalocid sodium, Levothyroxine, Linolenic acid, LOE-908, Loratadine, Lovastatin, Meclizine, Methacycline, Methylprednisolone, Metyrapone, Mevastatin, Mifepristone, Nafcillin, Nicardipine, Nicotine, Nifedipine, Nilvadipine, Nisoldipine, Norelgestromin, Omeprazole, Orlistat, Oxatomide, Paclitaxel, Phenobarbital, Plicamycin, Prednisolone, Pregnanolone, Pregnenolone, Pregnenolone 16α-carbonitrile, Proadifen, Progesterone, Reserpine, Reverse triiodothyronine Rifampicin, Rifaximin, Rimexolone, Riodipine, Ritonavir, Simvastatin, Sirolimus, Spironolactone, Spiroxatrine, SR-12813, Suberoylanilide, Sulfisoxazole, Suramin, Tacrolimus, Tenylidone, Terconazole, Testosterone isocaproate, Tetracycline, Thiamylal sodium, Thiothixene, Thonzonium bromide, Tianeptine, Troglitazone, Troleandomycin, Tropanyl 3,5-dimethulbenzoate, Zafirlukast, Zearalanol. PXR Antagonist such as Ketoconazole. RAR Agonists such as 9CDHRA, 9-cis-Retinoic acid (alitretinoin), AC-261066, AC-55649, Acitretin, Adapalene, all-trans-Retinoic acid (tretinoin), AM-580, BMS-493, BMS-753, BMS-961, CD-1530, CD-2314, CD-437, Ch-55, EC 23, Etretinate, Fenretinide, Isotretinoin, Palovarotene, Retinoic acid, Retinol (vitamin A), Tamibarotene, Tazarotene, Tazarotenic acid, TTNPB. RAR Antagonists such as BMS-195614, BMS-493, CD-2665, ER-50891, LE-135, MM-11253. RXR Agonists such as 9CDHRA, 9-cis-Retinoic acid (alitretinoin), all-trans-Retinoic acid (tretinoin), Bexarotene, CD 3254, Docosahexaenoic acid, Fluorobexarotene, Isotretinoin, LG-100268, LG-101506, LG-100754, Retinoic acid, Retinol (vitamin A), SR-11237. RXR Antagonists such as HX-531, HX-630, LG-100754, PA-452, UVI-3003. TR Agonists such as Dextrothyroxine, GC-1, Levothyroxine, Liothyronine, Thyroxine, Tiratricol, Triiodothyronine. Other compounds useful for modulation of NR2F6 activity include 5-tert-butyl-N-[(6-fluoro-4H-1,3-benzodioxin-8-yl)methyl]-2-methylpyrazole-3-carboxamide, ST50775950, ethyl 4-(cyclohexylamino)-2-(3,5-dimethylpyrazol-1-yl)pyrimidine-5-carboxylate, ethyl 4-(cyclopentylamino)-2-(3,5-dimethylpyrazol-1-yl)pyrimidine-5-carboxylate, AGN-PC-09SAX3, SMR000064686, AGN-PC-0NLTEQ, T6090485, MLS002548992, 5,6-dimethyl-4-[4-[2-(4-methylphenoxy)ethyl]piperazin-1-yl]thieno[2,3-d]pyrimidine, MLS002473459, MLS001030349, 4-(3,4-dihydro-1H-isoquinolin-2-yl)-5H-pyrimido[5,4-b]indole, 4-(3,4-Dihydro-1H-isoquinolin-2-yl)-8-fluoro-5H-pyrimido[5,4-b]indole, 4-[4-(4-methoxyphenyl)piperazino]-5H-pyrimido[5,4-b]indole, 4-[4-(1,3-benzodioxol-5-ylmethyl)piperazin-1-yl]-7-methoxy-5H-pyrimido[5,4-b]indole, SMR000044829, 8-fluoro-N-(3-propan-2-yloxypropyl)-5H-pyrimido [5,4-b]indol-4-amine, GNF-Pf-1678, MLS003116118, 2-[4-(5-methyl-[1,2,4]triazolo[1,5-a]pyrimidin-7-yl)piperazin-1-yl]-1,3-benzothiazole, 5-methyl-3,6-diphenylpyrazolo[1,5-a]pyrimidin-7-amine, 4-[4-[(4-chlorophenyl)methyl]piperazin-1-yl]-1-[(4-methylphenyl)methyl]pyrazolo[3,4-d]pyrimidine, MLS002632722, MLS002477203, MLS003120814, AGN-PC-07AHX3, MLS003120821, MLS003120807, MLS003120811, MLS003120820, ethyl 4-[[1-(2,4-dimethylphenyl)pyrazolo[3,4-d]pyrimidin-4-yl]amino]piperidine-1-carboxylate, N-[2-(3,4-dimethoxyphenyl)ethyl]thieno [2,3-d]pyrimidin-4-amine, N-[2-(3,4-dimethoxyphenyl)ethyl]-6-methylthieno [2,3-d]pyrimidin-4-amine hydrochloride, N-(1-phenylethyl)quinazolin-4-amine, AG-F-87638, ZINC03428816, CHEMBL493153, ST50323391, N-Benzylquinazolin-4-amine, ST50483228, N-[4-(2-methyl-1-methylsulfonyl-2,3-dihydroindol-5-yl)-1,3-thiazol-2-yl]-2-thiophen-2-ylacetamide, F0558-0175, AC1MLRO7, 4-(2-methylimidazo[1,2-a]pyridin-3-yl)-N-(3-methylphenyl)-1,3-thiazol-2-amine, AGN-PC-09PPXW, Compound 15Jf, AC1MEEXM, ST50941838, [2-[(3-carbamoylthiophen-2-yl)amino]-2-oxoethyl]2-naphthalen-1-ylacetate, F0239-0029, AC1OBZ0O, ST4126227, 1-[(4-bromophenyl)methyl]-2-methylbenzimidazole, SMR000718391, MLS002694437, Chlormidazole, 2-methyl-1-(2-methylbenzyl)-1H-benzimidazole, MLS003119103, Ambcb90456311, AGN-PC-04RX4B, MLS001122505, Ambcb81049924, AGN-PC-04RX7E, Ambcb42757923, MLS001124721, 7-benzyl-4-chloro-5,6-dimethyl-7H-pyrrolo[2,3-d]pyrimidine, AGN-PC-04V4GP, MLS000562030, AGN-PC-00YPMB, T5400648, MLS003107990, AC1NUNJE, MLS002701851, SMR000185185, STK850401, [(3-bromobenzyl) sulfanyl] [(4-fluorophenyl)amino]methylidene, propanedinitrile, AC1NXBLH, CAS-66-81-9, Cycloheximide, ACTIPHE- NOL, MLS001032885, MLS000553012, SMR000285129, MLS000688479, MLS002702480, GNF-Pf-4659, MLS002702449, T0501-4035, MLS000712179, AGN-PC-00MQWB, AGN-PC-0NKU3S, T0503-0850, T0501-5798, SMR000212173, 3,3'-Diethylthiazolinocarbocyanine iodide, 2-methyl-3,5-bis(4-methylphenyl)isoxazol-2-ium, MLS000705900, SMR000211540, AGN-PC-00PL3I, AGN-PC-0NJNZK, SMR000354849, T0503-1204, MLS000688685, GNF-Pf-4078, T0503-3525, T0503-4982, T0501-7391, GNF-Pf-3268, TCMDC-125620, 1-[1,1'-Biphenyl]-4-yl-2-(4-imino-1(4H)-pyridinyl)ethanone, SMR000036350, MLS000080109, MLS000080126, Ambcb40308772, MLS000733369, Ambcb20390854, MLS000732313, AGN-PC-04RYS6, Ambcb33735952, AGN-PC-04RYKA, MLS000733096, Ambcb63657849, MLS001090213, T6132867, MLS003678910, AC1OXF5M, SMR000218920, MLS000037490, Boc-KS, MLS000734694, AGN-PC-087SDW, ISUPSL100073, 4-{[5,7-bis(trifluoromethyl) benzenol, BAS 07204618, MLS001144057, MLS001250118, SMR000041809, SMR000635220, MLS003120011, T5546966, 4-chloro-N-(4-chlorobenzyl)-1,3-dimethyl-1H-pyrazole-5-carboxamide, 3-(Toluene-4-sulfonylmethyl)-2,3-dihydro-benzo [4,5] imidazo [2,1-b]thiazole, T0508-0735, Carboxyamidotriazole, MLS003116132, F0850-5968, Verrucarin A 9,10-epoxide, MLS002702133, Ossamycin, MLS002702060, Dihydrorotenone, SMR000623161, Pyridaben, ASN 09858385, T6069554, T6302989, SMR000629820, SMR000629835, MLS001028777, MLS001028747, MLS001028806, SMR000625125, T5403634, T5459762, T5626573, T5β37170, SMR000093473, T6120097, N-[2-[2-[2,5-dimethyl-1-(thiophen-2-ylmethyl)pyrrol-3-yl]-2-oxoethoxy]phenyl]acetamide, MLS000575323, N-[4-[2-[2,5-dimethyl-1-(thiophen-2-ylmethyl)pyrrol-3-yl]-2-oxoethyl]sulfanylphenyl] acetamide, SMR000274842, T5565081, 6-chloro-N-[3-[(4-methoxyphenyl)sulfamoyl]phenyl]pyridine-3-carboxamide, N-methyl-N-[(1,3,5-trimethylpyrazol-4-yl)methyl]naphthalene-2-sulfonamide, T6099016, T6094971, ASN 04448329, SMR000241542, AGN-PC-03RL0E, AGN-PC-080KFN, T6151837, AGN-PC-0KIUAY, N-[4-(4-methylphenyl)-1,3-thiazol-2-yl]-1-thiophen-2-ylsulfonylpiperidine-4-carboxamide, 5-(3,5-dimethylpiperidin-1-yl) sulfonyl-N,N-diethyl-3-methyl-1-benzofuran-2-carboxamide, SMR000124769, N-(1-benzylpiperidin-4-yl)-1-(5-chloro-2-methylphenyl) sulfonylpiperidine-4-carboxamide, MLS001095722, 4-ethoxy-N-(pyridin-4-ylmethyl)benzenesulfonamide, 4-chloro-3-ethoxy-N-(pyridin-4-ylmethyl) benzenesulfonamide, 2,4,6-trimethyl-N-(pyridin-4-ylmethyl)benzenesulfonamide, BAS 05598377, 4-bromo-2,5-dimethyl-N-(pyridin-4-ylmethyl)benzenesulfonamide, MLS000735463, MLS000687652, AGN-PC-093SBW, AG-401/42008258, 5L-526S, 2-[[5-(3-chloro-1-benzothiophen-2-yl)-1,3,4-oxadiazol-2-yl]sulfanyl]acetonitrile, 2-(5-Pyridin-3-yl-[1,3,4]thiadiazol-2-ylsulfanyl)-N-quinolin-4-yl-acetamide, 2-[[5-(benzotriazol-1-ylmethyl)-1,3,4-oxadiazol-2-yl]sulfanyl]-N-[(4-chlorophenyl)methyl]-N-phenylacetamide, 2-[[5-(benzotriazol-1-ylmethyl)-1,3,4-oxadiazol-2-yl]sulfanyl]-N-[(4-fluorophenyl)methyl]-N-phenylacetamide, SR-01000288264, 2-(1-cyclopropyltetrazol-5-yl) sulfanyl-1-[4-[(4-propan-2-ylphenyl)methyl]piperazin-1-yl]ethanone, N-(2,4-difluorophenyl)-4-[5-(trifluoromethyl)pyridin-2-yl]-1,4-diazepane-1-carbothioamide, T0512-9975, [[2,7-bis(2-morpholin-4-ylethoxy)fluoren-9-ylidene]amino]thiourea, MLS001018548, T0507-0244, 4-(4-acetylphenyl)-N-(4-phenoxyphenyl)piperazine-1-carbothioamide, N-(3-ethoxypropyl)-4-[4-(4-fluorophenyl)-1,3-thiazol-2-yl]piperazine-1-carbothioamide, (+)-Emetine dihydrochloride hydrate, MLS002302684, 4-(6-chloro-1,3-benzothiazol-2-yl)-N-(2-chloro-6-methylphenyl)-1,4-diazepane-1-carboxamide, N-(3-chloro-2-methylphenyl)-4-(3-phenyl-1,2,4-thiadiazol-5-yl)-1,4-diazepane-1-carboxamide, MLS000692856, bjm-csc-19, MLS002701991, and MLS000586514. Additional compounds include 6-formylindolo (3,2-B) carbazole, 4-hydroxyphenylretinamide, 3,5-Dilodo-L-tyrosine, Rifampicin, and Z30972355.

Another aspect of the present disclosure is a pharmaceutical composition comprising a NR2F6 modulator, such as a NR2F6 inhibitor or NR2F6 activator, for use in the methods described herein. Accordingly, the disclosure provides a pharmaceutical composition comprising an effective amount of a NR2F6 inhibitor or NR2F6 activator in admixture with a pharmaceutically acceptable carrier or diluent. In one embodiment, the pharmaceutical composition is used to inhibit NR2F6. In another embodiment, the pharmaceutical composition is used to activate NR2F6. In another embodiment, the pharmaceutical composition is used to treat hematopoietic conditions as described herein. The NR2F6 inhibitors or NR2F6 activators may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present disclosure is defined as an amount effective, at dosages and for periods of time necessary to achieve the desired result. For example, a therapeutically active amount of a substance may vary according to factors such as the disease state, age, sex, and weight of the individual, and the ability of inhibitor to elicit a desired response in the individual. Dosage regime may be adjusted to provide the optimum therapeutic response. For example, several divided doses may be administered daily or the dose may be proportionally reduced as indicated by the exigencies of the therapeutic situation. The active substance may be administered in a convenient manner such as by injection (subcutaneous, intravenous, intramuscular, etc.), oral administration, inhalation, intranasal, transdermal administration (such as topical cream or ointment, etc.), or suppository applications. In one embodiment, the active substance is administered by inhalation or intranasally. In another embodiment, the active substance is administered topically. Depending on the route of administration, the active substance may be coated in a material to protect the compound from the action of enzymes, acids and other natural conditions which may inactivate the compound. The active substance may be formulated into delayed release formulations such that NR2F6 can be inhibited or activated for longer periods of time than a conventional formulation. The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences (2000-20th edition) Mack Publishing Company). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Compositions disclosed in the current invention are useful for stimulation of immunity by derepressing inhibitory signals. In one embodiment, said compositions are useful in treatment of cancers, viral infections, bacterial infections, and other pathogen associated conditions. Stimulation of immunity is disclosed in the current invention through inhibition of NR2F6. In other situations inhibition of immunity is described by selection of compounds that enhance NR2F6 activity. Useful therapeutic uses of NR2F6 augmentation include the treatment of autoimmunity.

Example 1: Identification of Small Molecule Compounds Capable of Binding NR2F6

The binding interaction between target protein NR2F6 and 139 compounds selected from an in silico screen was assessed using thermoshift analysis (TSA). Thermoshift is a physical technique used to determine the melting temperature of a protein. The interaction of the ligand to the folded state of the protein shifts the melting temperature. In the experimental system used, the NR2F6 protein is mixed with the ligand and the fluorescent dye SYPRO Orange®. The fluorescence is monitored over temperature gradient between 20 and 95° C. with 0.5° C. increment. The dye binds to the hydrophobic regions of molten globules and denatured proteins resulting in an increase of fluorescence. A plot of the fluorescence is obtained and used to determine the melting temperature in absence and presence of ligand.

The ligand binding domain of NR2F6 (amino acids 163-404) was cloned for soluble expression in E. coli with an N-terminal HIS-FLAG-TEV-tag. Expression was performed in BL21 (DE3) cells. In brief, a 12L E. coli culture was induced with IPTG in logarithmic phase and further incubated over night at 18° C. Cells were harvested via centrifugation, washed with buffer and stored at 20° C. until purification.

The purification procedure performed consists of HIS affinity chromatography, tag cleavage, negative affinity chromatography, size exclusion chromatography and ion exchange chromatography. The resulting NR2F6 was concentrated on a 10 kD Vivascience ultrafiltration device to a final concentration of ~4 mg/ml with a purity of >90%.

Thermoshift analysis was performed on 139 Compounds that were stored as powder in DMSO stocks. A reaction volume of 25 µl was used, with reaction temperatures being increased in 0.5 increments from 20-95° C. in 96 well, PCR plates (Hard-Shell®, HSP-9655). The control was NR2F6 protein alone in 1% DMSO. For performing the reaction, a reaction buffer comprising of the following was utilized: 20 mM HEPES pH 6.85, 150 mM NaCl, 10% Glycerin and 0.5 mM TCEP. The final concentrations of the experiments were 0.5 mg/ml NR2F6, 100 µM compound (1% DMSO), 25×SYPRO Orange® (Some compounds showed high fluorescence and had to be tested using lower SYPRO Orange® concentration).

The following pipetting sequence was used: 1) Add appropriate volume of target enzyme in reaction buffer; 2) Add appropriate volume of dye SYPRO Orange® in reaction buffer; 3) Add inhibitor in 100% DMSO (1% final DMSO conc); 4) Measure fluorescence Fluorescence was quantified using a CFX Connect™ Real-Time PCR Detection System (BioRad)

In the absence of test compound the protein NR2F6 shows a melting temperature (Tm) of 48° C. Seven out of the 139 compounds shifted the melting temperature at least 1° C. to higher melting temperatures (Table 1.1). For 10 out of the 139 compounds a shift of at least 1.5° C. to lower Tm values were observed.

An increase in melting temperature is indicative for compound binding. The larger the melting temperature shift, the higher is the verification rate in subsequent orthogonal ITC profiling steps. However a melting temperature decrease can be caused by either a regular compound binding to the protein but also by compound induced denaturation of the protein. Thus compounds with an increase of Tm verify more frequently than compounds with a reduction in Tm. In order to increase the chance for a high ITC verification rate the 5 compounds with the largest Tm increase were recommended to be ITC profiled with priority. Data and compound structure for these 5 compounds are summarized in tables 1.2 and 1.3. The remaining 2 compounds with Tm increase and the 10 compounds with Tm decrease were recommended for ITC profiled with priority 2.

TABLE 1.1

Summary of Tm Values

| Cpd N. | Compound ID | compound conc [µM] | Tm [° C.] | delta Tm [° C.] | Comment | Recommended for ITC |
|---|---|---|---|---|---|---|
| 61 | Bezafibrate | 100 | 48 | 0 | | |
| 62 | GW 9662 | 100 | 48 | 0 | | |
| 63 | Glycochalic acid | 100 | 48 | 0 | | |
| 64 | Z-Guggulsterone | 100 | 46 | −2 | | priority 2 |
| 65 | 17b-Estradiol | 100 | 47 | −1 | | |
| 66 | WY-14643 | 100 | 47.5 | −0.5 | | |
| 67 | LY 171883 | 100 | 46.5 | −1.5 | | |
| 68 | Gemfibrozil | 100 | 47.5 | −0.5 | | |
| 69 | Glycodeoxycholic acid | 100 | 46.5 | −1.5 | | |
| 70 | TCPOBOP | 100 | 48 | 0 | | |
| 71 | Pregnenoione | 100 | 48 | 0 | | |
| 72 | Ciglitazone | 100 | 47.5 | −0.5 | | |
| 73 | 15-Deoxy-D12, 14-prostaglandin J2 | 100 | 48 | 0 | | |
| 74 | GW 7647 | 100 | 45.5 | −2.5 | | priority 2 |
| 75 | Taurocholic acid | 100 | 47.5 | −0.5 | | |
| 76 | N-Oleoylethanolamide | 100 | 48.5 | 0.5 | | |
| 77 | Androstenedione | 100 | 47 | −1 | | |

TABLE 1.1-continued

Summary of Tm Values

| Cpd N. | Compound ID | compound conc [μM] | Tm [° C.] | delta Tm [° C.] | Comment | Recommended for ITC |
|---|---|---|---|---|---|---|
| 78 | Tetradecylthioacetic acid | 100 | 49.5 | 1.5 | cpd interference | |
| 79 | Troglitazone | 100 | 48 | 0 | | |
| 80 | 3,5-Diiodo-L-thyroine | 100 | 48.5 | 0.5 | | |
| 81 | Taurodeoxycholic acid | 100 | 47.5 | −0.5 | | |
| 82 | GW4064 | 100 | 35 | −13 | cpd interference | |
| 83 | 1a,25-Dihydroxyvitamin D3 | 100 | 46.5 | −1.5 | | |
| 84 | 5,8,11,14-Eicosatetranoic acid | 100 | 46.5 | −1.5 | cpd interference | |
| 85 | CITCO | 100 | 48 | 0 | | |
| 86 | 3,5-Diiodo-L-tyrosine | 100 | 50 | 2 | | priority 1 |
| 87 | Rifampicin | 100 | 49.5 | 1.5 | | priority 1 |
| 88 | Geranylgeranoil | 100 | 47.5 | −0.5 | | |
| 89 | Docosa-4Z,7Z,10Z,13Z,16Z,19Z-hexaenoic acid | 100 | 47.5 | −0.5 | | |
| 90 | 5120656 | 100 | 49 | 1 | | priority 2 |
| 91 | 5350713 | 100 | 48 | 0 | | |
| 92 | 5567167 | 100 | 46 | −2 | | priority 2 |
| 93 | 5646978 | 100 | 48 | 0 | | |
| 94 | 5813525 | 100 | 47 | −1 | | |
| 95 | 5932607 | 100 | 47.5 | −0.5 | | |
| 96 | 6484065 | 100 | 48 | 0 | | |
| 97 | 6694921 | 100 | 48.5 | 0.5 | | |
| 98 | 6815135 | 100 | 48 | 0 | | |
| 99 | 6957469 | 100 | 48 | 0 | | |
| 100 | 7232897 | 100 | 46.5 | −1.5 | | |
| 101 | 7273895 | 100 | 48 | 0 | | |
| 102 | 7801931 | 100 | 47.5 | −0.5 | | |
| 103 | 7850189 | 100 | 47.5 | −0.5 | | |
| 104 | 7960292 | 100 | 48 | 0 | | |
| 105 | 7986450 | 100 | 48 | 0 | | |
| 106 | 7989029 | 100 | 48 | 0 | | |
| 107 | 8800862 | 100 | 48 | 0 | | |
| 108 | 8906332 | 100 | 47.5 | −0.5 | | |
| 109 | 9001748 | 100 | 48 | 0 | | |
| 110 | 9112600 | 100 | 46 | −2 | | priority 2 |
| 111 | 22252122 | 100 | 47.5 | −0.5 | | |
| 112 | 26679136 | 100 | 46 | −2 | | priority 2 |
| 113 | 42757923 | 100 | 48 | 0 | | |
| 114 | 55536813 | 100 | 47.5 | −0.5 | | |
| 115 | 90456311 | 100 | 47 | −1 | | |
| 116 | Z31759534 | 100 | 47.5 | −0.5 | | |
| 117 | Z30824658 | 100 | 48.5 | 0.5 | | |
| 118 | Z27623551 | 100 | 47.5 | −0.5 | | |
| 119 | Z19816924 | 100 | 46 | −2 | | priority 2 |
| 120 | Z52581254 | 100 | 46.5 | −1.5 | | |
| 121 | Z15516503 | 100 | 48 | 0 | | |
| 122 | Z19316285 | 100 | 47.5 | −0.5 | | |
| 123 | Z15517610 | 100 | 47.5 | −0.5 | | |
| 124 | Z26334198 | 100 | 46 | −2 | | priority 2 |
| 125 | Z53796578 | 100 | 47.5 | −0.5 | | |
| 126 | Z127091022 | 100 | 47.5 | −0.5 | | |
| 127 | Z52035862 | 100 | 47.5 | −0.5 | | |
| 128 | Z21509585 | 100 | 48 | 0 | | |
| 129 | Z31152558 | 100 | 47.5 | −0.5 | | |
| 130 | Z223824560 | 100 | 47.5 | −0.5 | | |
| 131 | Z45883881 | 100 | 47.5 | −0.5 | | |
| 132 | Z85517717 | 100 | 47.5 | −0.5 | | |
| 133 | Z30972366 | 100 | 49 | 1 | | priority 1 |
| 134 | Z57161635 | 100 | 47.5 | −0.5 | | |
| 135 | Z87546818 | 100 | 47.5 | −0.5 | | |
| 136 | Z45800144 | 100 | 47.5 | −0.5 | | |
| 137 | Z48569117 | 100 | 48 | 0 | | |
| 138 | Z26013519 | 100 | 46 | −2 | | |
| 139 | Z15517731 | 100 | 48.5 | 0.5 | | |

TABLE 1.2

Summary of Compounds Capable of Modulating NR2F6

| Cpd N. | Compound ID | compound conc [μM] | Tm [° C.] |
|---|---|---|---|
| 17 | 6-Formylindolo [3,2-B] carbazole | 100 | 50 |
| 43 | 4-Hydroxyphenylretinamide | 100 | 50 |
| 86 | 3,5-Diiodo-L-tyrosine | 100 | 50 |

TABLE 1.2-continued

Summary of Compounds Capable of Modulating NR2F6

| Cpd N. | Compound ID | compound conc [μM] | Tm [° C.] |
|---|---|---|---|
| 87 | Rifampicin | 100 | 49.5 |
| 133 | Z30972366 | 100 | 49 |

TABLE 1.3

Structure of Compounds Capable of Modulating NR2F6

| Cpd N. | Compound ID | Structure |
|---|---|---|
| 17 | 6-Formylindolo[3,2-B] carbazole | *(structure)* |
| 43 | 4-Hydroxyphenylretinamide | *(structure)* |
| 86 | 3,5-Diiodo-L-tyrosine | *(structure)* |
| 87 | Rifampicin | *(structure)* |
| 133 | Z30972366 | *(structure)* |

REFERENCES

1. McCoy, K. D. and G. Le Gros, *The role of CTLA-4 in the regulation of T cell immune responses*. Immunol Cell Biol, 1999. 77(1): p. 1-10.
2. Bretscher, P., *The two-signal model of lymphocyte activation twenty-one years later*. Immunol Today, 1992. 13(2): p. 74-6.
3. Bretscher, P. and M. Cohn, *A theory of self-nonself discrimination*. Science, 1970. 169(3950): p. 1042-9.
4. Damle, N. K., et al., *Differential regulatory signals delivered by antibody binding to the CD28 (Tp44) molecule during the activation of human T lymphocytes*. J Immunol, 1988. 140(6): p. 1753-61.
5. Ledbetter, J. A., et al., *CD28 ligation in T-cell activation: evidence for two signal transduction pathways*. Blood, 1990. 75(7): p. 1531-9.
6. Linsley, P. S., et al., *Binding of the B cell activation antigen B7 to CD28 costimulates T cell proliferation and interleukin 2 mRNA accumulation*. J Exp Med, 1991. 173(3): p. 721-30.
7. Scalapino, K. J. and D. I. Daikh, *CTLA-4: a key regulatory point in the control of autoimmune disease*. Immunol Rev, 2008. 223: p. 143-55.
8. Chin, L. T., et al., *Immune intervention with monoclonal antibodies targeting CD152 (CTLA-4) for autoimmune and malignant diseases*. Chang Gung Med J, 2008. 31(1): p. 1-15.
9. O'Day, S. J., O. Hamid, and W. J. Urba, *Targeting cytotoxic T-lymphocyte antigen-4 (CTLA-4): a novel strategy for the treatment of melanoma and other malignancies*. Cancer, 2007. 110(12): p. 2614-27.
10. Riley, J. L., *PD-1 signaling in primary T cells*. Immunol Rev, 2009. 229(1): p. 114-25.
11. Chemnitz, J. M., et al., *SHP-1 and SHP-2 associate with immunoreceptor tyrosine-based switch motif of programmed death 1 upon primary human T cell stimulation, but only receptor ligation prevents T cell activation*. J Immunol, 2004. 173(2): p. 945-54.
12. Marelli-Berg, F. M., et al., *The highway code of T cell trafficking*. J Pathol, 2008. 214(2): p. 179-89.
13. Safe, S., et al., *Minireview: role of orphan nuclear receptors in cancer and potential as drug targets*. Mol Endocrinol, 2014. 28(2): p. 157-72.
14. Sonoda, J., L. Pei, and R. M. Evans, *Nuclear receptors: decoding metabolic disease*. FEBS Lett, 2008. 582(1): p. 2-9.
15. Bookout, A. L., et al., *Anatomical profiling of nuclear receptor expression reveals a hierarchical transcriptional network*. Cell, 2006. 126(4): p. 789-99.
16. Evans, R. M., *The nuclear receptor superfamily: a rosetta stone for physiology*. Mol Endocrinol, 2005. 19(6): p. 1429-38.
17. Mangelsdorf, D. J., et al., *The nuclear receptor superfamily: the second decade*. Cell, 1995. 83(6): p. 835-9.
18. Katzenellenbogen, J. A., B. W. O'Malley, and B. S. Katzenellenbogen, *Tripartite steroid hormone receptor pharmacology: interaction with multiple effector sites as a basis for the cell- and promoter-specific action of these hormones*. Mol Endocrinol, 1996. 10(2): p. 119-31.
19. Sundahl, N., et al., *Selective glucocorticoid receptor modulation: New directions with non-steroidal scaffolds*. Pharmacol Ther, 2015. 152: p. 28-41.
20. Bouchard, P., *Selective progesterone receptor modulators: a class with multiple actions and applications in reproductive endocrinology, and gynecology*. Gynecol Endocrinol, 2014. 30(10): p. 683-4.
21. Whitaker, L. H., A. R. Williams, and H. O. Critchley, *Selective progesterone receptor modulators*. Curr Opin Obstet Gynecol, 2014. 26(4): p. 237-42.
22. Yamada, S. and M. Makishima, *Structure-activity relationship of nonsecosteroidal vitamin D receptor modulators*. Trends Pharmacol Sci, 2014. 35(7): p. 324-37.
23. Burris, T. P., et al., *Nuclear receptors and their selective pharmacologic modulators*. Pharmacol Rev, 2013. 65(2): p. 710-78.
24. Jordan, V. C., *SERMs: meeting the promise of multifunctional medicines*. J Natl Cancer Inst, 2007. 99(5): p. 350-6.
25. Jordan, V. C. and B. W. O'Malley, *Selective estrogen-receptor modulators and antihormonal resistance in breast cancer*. J Clin Oncol, 2007. 25(36): p. 5815-24.
26. Jordan, V. C., *Antiestrogens and selective estrogen receptor modulators as multifunctional medicines. 1. Receptor interactions*. J Med Chem, 2003. 46(6): p. 883-908.
27. Jordan, V. C., *Antiestrogens and selective estrogen receptor modulators as multifunctional medicines. 2. Clinical considerations and new agents*. J Med Chem, 2003. 46(7): p. 1081-111.
28. Zhang, X., H. Zhou, and Y. Su, *Targeting truncated RXRalpha for cancer therapy*. Acta Biochim Biophys Sin (Shanghai), 2015.
29. Thomas, M., M. A. Sukhai, and S. Kamel-Reid, *An emerging role for retinoid X receptor alpha in malignant hematopoiesis*. Leuk Res, 2012. 36(9): p. 1075-81.
30. le Maire, A., et al., *Retinoid receptors and therapeutic applications of RAR/RXR modulators*. Curr Top Med Chem, 2012. 12(6): p. 505-27.
31. Dawson, M. I. and Z. Xia, *The retinoid X receptors and their ligands*. Biochim Biophys Acta, 2012. 1821(1): p. 21-56.
32. Tabe, Y., et al., *Effects of PPARgamma Ligands on Leukemia*. PPAR Res, 2012. 2012: p. 483656.
33. Tabe, Y., et al., *PPARgamma-active triterpenoid CDDO enhances ATRA-induced differentiation in APL*. Cancer Biol Ther, 2007. 6(12): p. 1967-77.
34. Koutsounas, I., E. Patsouris, and S. Theocharis, *Pregnane X receptor and human malignancy*. Histol Histopathol, 2013. 28(4): p. 405-20.
35. Chatagnon, A., et al., *RAR/RXR binding dynamics distinguish pluripotency from differentiation associated cis-regulatory elements*. Nucleic Acids Res, 2015. 43(10): p. 4833-54.
36. Guan, H. B., et al., *Acyclic retinoid induces differentiation and apoptosis of murine hepatic stem cells*. Stem Cell Res Ther, 2015. 6: p. 51.
37. Papi, A., et al., *PPARgamma and RXR ligands disrupt the inflammatory cross-talk in the hypoxic breast cancer stem cells niche*. J Cell Physiol, 2014. 229(11): p. 1595-606.
38. Papi, A., et al., *Nuclear receptors agonists exert opposing effects on the inflammation dependent survival of breast cancer stem cells*. Cell Death Differ, 2012. 19(7): p. 1208-19.
39. Iliopoulos, D., A. Rotem, and K. Struhl, *Inhibition of miR-193a expression by Max and RXRalpha activates K-Ras and PLA U to mediate distinct aspects of cellular transformation*. Cancer Res, 2011. 71(15): p. 5144-53.
40. He, B. C., et al., *Synergistic antitumor effect of the activated PPARgamma and retinoid receptors on human osteosarcoma*. Clin Cancer Res, 2010. 16(8): p. 2235-45.
41. Willhauck, M. J., et al., *Stimulation of retinoic acid-induced functional sodium iodide symporter (NIS) expres- 41. ...sion and cytotoxicity of (1)(3)(1)1 by carbamazepine in breast cancer cells. Breast Cancer Res Treat, 2011. 125(2): p. 377-86.
42. Kashyap, V. and L. J. Gudas, *Epigenetic regulatory mechanisms distinguish retinoic acid-mediated transcriptional responses in stem cells and fibroblasts.* J Biol Chem, 2010. 285(19): p. 14534-48.
43. Qiu, J. J., et al., *Leukemic transformation by the APL fusion protein PRKARIA-RAR{alpha} critically depends on recruitment of RXR{alpha}.* Blood, 2010. 115(3): p. 643-52.
44. Papi, A., et al., *PPARgamma and RXRgamma ligands act synergistically as potent antineoplastic agents in vitro and in vivo glioma models.* J Neurochem, 2009. 109(6): p. 1779-90.
45. Safi, R., et al., *Pharmacological manipulation of the RAR/RXR signaling pathway maintains the repopulating capacity of hematopoietic stem cells in culture.* Mol Endocrinol, 2009. 23(2): p. 188-201.
46. Nieto-Rementeria, N., et al., *Bexarotene activates the p53/p73 pathway in human cutaneous T-cell lymphoma.* Br J Dermatol, 2009. 160(3): p. 519-26.
47. Su, D. and L. J. Gudas, *Retinoic acid receptor gamma activates receptor tyrosine kinase Tie1 gene transcription through transcription factor GATA4 in F9 stem cells.* Exp Hematol, 2008. 36(5): p. 624-41.
48. Su, D. and L. J. Gudas, *Gene expression profiling elucidates a specific role for RARgamma in the retinoic acid-induced differentiation of F9 teratocarcinoma stem cells.* Biochem Pharmacol, 2008. 75(5): p. 1129-60.
49. Zhou, J., et al., *Dimerization-induced corepressor binding and relaxed DNA-binding specificity are critical for PML/RARA-induced immortalization.* Proc Natl Acad Sci USA, 2006. 103(24): p. 9238-43.
50. Kogai, T., et al., *Differential regulation of sodium/iodide symporter gene expression by nuclear receptor ligands in MCF-7 breast cancer cells.* Endocrinology, 2005. 146(7): p. 3059-69.
51. Manfredini, R., et al., *Induction of a functional vitamin D receptor in all-trans-retinoic acid-induced monocytic differentiation of M2-type leukemic blast cells.* Cancer Res, 1999. 59(15): p. 3803-11.
52. Prost, S., et al., *Erosion of the chronic myeloid leukaemia stem cell pool by PPARgamma agonists.* Nature, 2015. 525(7569): p. 380-3.
53. Wang, Y., et al., *The combinatory effects of PPAR-gamma agonist and survivin inhibition on the cancer stem-like phenotype and cell proliferation in bladder cancer cells.* Int J Mol Med, 2014. 34(1): p. 262-8.
54. Kim, T. I., *Chemopreventive drugs: mechanisms via inhibition of cancer stem cells in colorectal cancer.* World J Gastroenterol, 2014. 20(14): p. 3835-46.
55. Chu, T. H., et al., *Celecoxib suppresses hepatoma stemness and progression by up-regulating PTEN.* Oncotarget, 2014. 5(6): p. 1475-90.
56. Liu, L., et al., *Inhibition of oxidative stress-elicited AKT activation facilitates PPARgamma agonist-mediated inhibition of stem cell character and tumor growth of liver cancer cells.* PLoS One, 2013. 8(8): p. e73038.
57. Moon, C. M., et al., *Nonsteroidal anti-inflammatory drugs suppress cancer stem cells via inhibiting PTGS2 (cyclooxygenase 2) and NOTCH/HES1 and activating PPARG in colorectal cancer.* Int J Cancer, 2014. 134(3): p. 519-29.
58. Wang, X., et al., *PPARgamma maintains ERBB2-positive breast cancer stem cells.* Oncogene, 2013. 32(49): p. 5512-21.
59. Papi, A., et al., *Peroxisome proliferator activated receptor-alpha/hypoxia inducible factor-1alpha interplay sustains carbonic anhydrase IX and apolipotrotein E expression in breast cancer stem cells.* PLoS One, 2013. 8(1): p. e54968.
60. Han, E. J., et al., *Combined treatment with peroxisome proliferator-activated receptor (PPAR) gamma ligands and gamma radiation induces apoptosis by PPARgamma-independent up-regulation of reactive oxygen species-induced deoxyribonucleic acid damage signals in non-small cell lung cancer cells.* Int J Radiat Oncol Biol Phys, 2013. 85(5): p. e239-48.
61. Kimura, O., Y. Kondo, and T. Shimosegawa, *PPAR Could Contribute to the Pathogenesis of Hepatocellular Carcinoma.* PPAR Res, 2012. 2012: p. 574180.
62. Zhan, L., et al., *Regulatory role of KEAP1 and NRF2 in PPARgamma expression and chemoresistance in human non-small-cell lung carcinoma cells.* Free Radic Biol Med, 2012. 53(4): p. 758-68.
63. Galzio, R., et al., *Hypoxia modulation of peroxisome proliferator-activated receptors (PPARs) in human glioblastoma stem cells. Implications for therapy.* J Cell Biochem, 2012. 113(11): p. 3342-52.
64. Li, T., et al., *Pseudolaric acid B inhibits T-cell mediated immune response in vivo via p38MAPK signal cascades and PPARgamma activation.* Life Sci, 2015. 121: p. 88-96.
65. Khare, A., et al., *Cutting Edge: Dual Function of PPARgamma in CD11c+ Cells Ensures Immune Tolerance in the Airways.* J Immunol, 2015. 195(2): p. 431-5.
66. Rao, E., et al., *Targeting epidermal fatty acid binding protein for treatment of experimental autoimmune encephalomyelitis.* BMC Immunol, 2015. 16: p. 28.
67. Adhikary, T., et al., *The transcriptional PPARbeta/delta network in human macrophages defines a unique agonist-induced activation state.* Nucleic Acids Res, 2015. 43(10): p. 5033-51.
68. Tan, P. H., et al., *Adiponectin receptor signaling on dendritic cells blunts antitumor immunity.* Cancer Res, 2014. 74(20): p. 5711-22.
69. Ferrari, S. M., et al., *Modulatory effects of peroxisome proliferator-activated receptor-gamma on CXCR3 chemokines.* Recent Pat Inflamm Allergy Drug Discov, 2014. 8(2): p. 132-8.
70. Wang, B., et al., *Resveratrol prevents suppression of regulatory T-cell production, oxidative stress, and inflammation of mice prone or resistant to high-fat diet-induced obesity.* Nutr Res, 2013. 33(11): p. 971-81.
71. von Knethen, A., et al., *5-Lipoxygenase contributes to PPARgamma activation in macrophages in response to apoptotic cells.* Cell Signal, 2013. 25(12): p. 2762-8.
72. da Rocha Junior, L. F., et al., *PPARgamma Agonists in Adaptive Immunity: What Do Immune Disorders and Their Models Have to Tell Us?* PPAR Res, 2013. 2013: p. 519724.
73. Jaudszus, A., et al., *Evaluation of suppressive and pro-resolving effects of EPA and DHA in human primary monocytes and T-helper cells.* J Lipid Res, 2013. 54(4): p. 923-35.
74. Cipolletta, D., et al., *PPAR-gamma is a major driver of the accumulation and phenotype of adipose tissue Treg cells.* Nature, 2012. 486(7404): p. 549-53.
75. Norazmi, M. N., et al., *The modulation of PPARgamma1 and PPARgamma2 mRNA expression by ciglitazone in CD3/CD28-activated naive and memory CD4+ T cells.* Clin Dev Immunol, 2012. 2012: p. 849195.

76. Housley, W. J., et al., *Peroxisome proliferator-activated receptor gamma is required for CD4+ T cell-mediated lymphopenia-associated autoimmunity.* J Immunol, 2011. 187(8): p. 4161-9.
77. Iwami, D., et al., *Immunomodulatory effects of eicosapentaenoic acid through induction of regulatory T cells.* Int Immunopharmacol, 2011. 11(3): p. 384-9.
78. Antonelli, A., et al., *CXCL9 and CXCL11 chemokines modulation by peroxisome proliferator-activated receptor-alpha agonists secretion in Graves' and normal thyrocytes.* J Clin Endocrinol Metab, 2010. 95(12): p. E413-20.
79. Majai, G., et al., *PPARgamma modulated inflammatory response of human dendritic cell subsets to engulfed apoptotic neutrophils.* J Leukoc Biol, 2010. 88(5): p. 981-91.
80. Dunn, S. E., et al., *Peroxisome proliferator-activated receptor delta limits the expansion of pathogenic Th cells during central nervous system autoimmunity.* J Exp Med, 2010. 207(8): p. 1599-608.
81. Guri, A. J., et al., *The role of T cell PPAR gamma in mice with experimental inflammatory bowel disease.* BMC Gastroenterol, 2010. 10: p. 60.
82. Kanakasabai, S., et al., *Peroxisome proliferator-activated receptor delta agonists inhibit T helper type 1 (Th1) and Th17 responses in experimental allergic encephalomyelitis.* Immunology, 2010. 130(4): p. 572-88.
83. Klotz, L., et al., *Increased antigen cross-presentation but impaired cross-priming after activation of peroxisome proliferator-activated receptor gamma is mediated by up-regulation of B7H1.* J Immunol, 2009. 183(1): p. 129-36.
84. Trigunaite, A., J. Dimo, and T. N. Jorgensen, *Suppressive effects of androgens on the immune system.* Cell Immunol, 2015. 294(2): p. 87-94.
85. Gutsol, A. A., et al., *[The influence of testosterone and beta-estradiol on T-lymphocytes activation associated with IL-2 production and expression of CD25 (IL-2Ralpha) molecules].* Tsitologiia, 2014. 56(7): p. 500-3.
86. Ardiani, A., et al., *Androgen deprivation therapy sensitizes prostate cancer cells to T-cell killing through androgen receptor dependent modulation of the apoptotic pathway.* Oncotarget, 2014. 5(19): p. 9335-48.
87. Velardi, E., et al., *Sex steroid blockade enhances thymopoiesis by modulating Notch signaling.* J Exp Med, 2014. 211(12): p. 2341-9.
88. Kissick, H. T., et al., *Androgens alter T-cell immunity by inhibiting T-helper 1 differentiation.* Proc Natl Acad Sci USA, 2014. 111(27): p. 9887-92.
89. Fan, Y., et al., *Low intraprostatic DHT promotes the infiltration of CD8+ T cells in BPH tissues via modulation of CCL5 secretion.* Mediators Inflamm, 2014. 2014: p. 397815.
90. Vignozzi, L., et al., *Antiinflammatory effect of androgen receptor activation in human benign prostatic hyperplasia cells.* J Endocrinol, 2012. 214(1): p. 31-43.
91. Yang, L., et al., *Relationship between the anti-inflammatory properties of salmeterol/fluticasone and the expression of CD4(+)CD25(+)Foxp3(+) regulatory T cells in COPD.* Respir Res, 2011. 12: p. 142.
92. Radojevic, K., et al., *Neonatal androgenization affects the efficiency of beta-adrenoceptor-mediated modulation of thymopoiesis.* J Neuroimmunol, 2011. 239(1-2): p. 68-79.
93. Frisancho-Kiss, S., et al., *Gonadectomy of male BALB/c mice increases Tim-3(+) alternatively activated M2 macrophages, Tim-3(+) T cells, Th2 cells and Treg in the heart during acute coxsackievirus-induced myocarditis.* Brain Behav Immun, 2009. 23(5): p. 649-57.
94. Yan, W. and H. H. Tai, *Glycogen synthase kinase-3 phosphorylation, T-cell factor signaling activation, and cell morphology change following stimulation of thromboxane receptor alpha.* J Pharmacol Exp Ther, 2006. 317(1): p. 267-74.
95. Page, S. T., et al., *Effect of medical castration on CD4+ CD25+ T cells, CD8+ T cell IFN-gamma expression, and NK cells: a physiological role for testosterone and/or its metabolites.* Am J Physiol Endocrinol Metab, 2006. 290(5): p. E856-63.
96. Chahar, S., et al., *Chromatin profiling reveals regulatory network shifts and a protective role for hepatocyte nuclear factor 4alpha during colitis.* Mol Cell Biol, 2014. 34(17): p. 3291-304.
97. Farhat, A., et al., *Tris(1,3-dichloro-2-propyl) phosphate perturbs the expression of genes involved in immune response and lipid and steroid metabolism in chicken embryos.* Toxicol Appl Pharmacol, 2014. 275(2): p. 104-12.
98. Shavva, V. S., et al., *Hepatic nuclear factor 4alpha positively regulates complement C3 expression and does not interfere with TNFalpha-mediated stimulation of C3 expression in HepG2 cells.* Gene, 2013. 524(2): p. 187-92.
99. Wang, X. X., T. Jiang, and M. Levi, *Nuclear hormone receptors in diabetic nephropathy.* Nat Rev Nephrol, 2010. 6(6): p. 342-51.
100. Bolotin, E., et al., *Integrated approach for the identification of human hepatocyte nuclear factor 4alpha target genes using protein binding microarrays.* Hepatology, 2010. 51(2): p. 642-5β.
101. Darsigny, M., et al., *Loss of hepatocyte-nuclear-factor-4alpha affects colonic ion transport and causes chronic inflammation resembling inflammatory bowel disease in mice.* PLoS One, 2009. 4(10): p. e7609.
102. Osanai, M., et al., *Hepatocyte nuclear factor (HNF)-4alpha induces expression of endothelial Fas ligand (FasL) to prevent cancer cell transmigration: a novel defense mechanism of endothelium against cancer metastasis.* Jpn J Cancer Res, 2002. 93(5): p. 532-41.
103. Talaber, G., M. Jondal, and S. Okret, *Extra-adrenal glucocorticoid synthesis: immune regulation and aspects on local organ homeostasis.* Mol Cell Endocrinol, 2013. 380(1-2): p. 89-98.
104. Sidler, D., et al., *Colon cancer cells produce immunoregulatory glucocorticoids.* Oncoimmunology, 2012. 1(4): p. 529-530.
105. El-Karaksy, S. M., et al., *Down-regulation of expression of retinoid acid-related orphan receptor C (RORC) in systemic lupus erythematosus.* J Recept Signal Transduct Res, 2015: p. 1-6.
106. Yang, B. H., et al., *Foxp3 T cells expressing RORgammat represent a stable regulatory T-cell effector lineage with enhanced suppressive capacity during intestinal inflammation.* Mucosal Immunol, 2015.
107. Kojima, H., et al., *Isoflavones enhance interleukin-17 gene expression via retinoic acid receptor-related orphan receptors alpha and gamma.* Toxicology, 2015. 329: p. 32-9.
108. Solt, L. A., et al., *ROR inverse agonist suppresses insulitis and prevents hyperglycemia in a mouse model of type 1 diabetes.* Endocrinology, 2015. 156(3): p. 869-81.
109. Yang, Y., et al., *Impact of suppressing retinoic acid-related orphan receptor gamma t (ROR)gammat in ameliorating central nervous system autoimmunity.* Clin Exp Immunol, 2015. 179(1): p. 108-18.

110. Martinez, N. E., et al., *Th17-biased RORgammat transgenic mice become susceptible to a viral model for multiple sclerosis.* Brain Behav Immun, 2015. 43: p. 86-97.
111. Chang, M. R., H. Rosen, and P. R. Griffin, *RORs in autoimmune disease.* Curr Top Microbiol Immunol, 2014. 378: p. 171-82.
112. Bidad, K., et al., *Effect of all-transretinoic acid on Th17 and T regulatory cell subsets in patients with ankylosing spondylitis.* J Rheumatol, 2013. 40(4): p. 476-83.
113. Jetten, A. M., H. S. Kang, and Y. Takeda, *Retinoic acid-related orphan receptors alpha and gamma: key regulators of lipid/glucose metabolism, inflammation, and insulin sensitivity.* Front Endocrinol (Lausanne), 2013. 4: p. 1.
114. Muranski, P. and N. P. Restifo, *Essentials of Th17 cell commitment and plasticity.* Blood, 2013. 121(13): p. 2402-14.
115. Huh, J. R. and D. R. Littman, *Small molecule inhibitors of RORgammat: targeting Th17 cells and other applications.* Eur J Immunol, 2012. 42(9): p. 2232-7.
116. Wang, Z., et al., *Structure and function of Nurr1 identifies a class of ligand-independent nuclear receptors.* Nature, 2003. 423(6939): p. 555-60.
117. Nagy, L. and J. W. Schwabe, *Mechanism of the nuclear receptor molecular switch.* Trends Biochem Sci, 2004. 29(6): p. 317-24.
118. Li, Y., M. H. Lambert, and H. E. Xu, *Activation of nuclear receptors: a perspective from structural genomics.* Structure, 2003. 11(7): p. 741-6.
119. Muscat, G. E., et al., *Research resource: nuclear receptors as transcriptome: discriminant and prognostic value in breast cancer.* Mol Endocrinol, 2013. 27(2): p. 350-65.
120. Jeong, Y., et al., *Research resource: Diagnostic and therapeutic potential of nuclear receptor expression in lung cancer.* Mol Endocrinol, 2012. 26(8): p. 1443-54.
121. Jeong, Y., et al., *Nuclear receptor expression defines a set of prognostic biomarkers for lung cancer.* PLoS Med, 2010. 7(12): p. e1000378.
122. Holbeck, S., et al., *Expression profiling of nuclear receptors in the NCI60 cancer cell panel reveals receptor-drug and receptor-gene interactions.* Mol Endocrinol, 2010. 24(6): p. 1287-96.
123. Li, X. B., et al., *The orphan nuclear receptor EAR2 is overexpressed in colorectal cancer and it regulates survivability of colon cancer cells.* Cancer Lett, 2011. 309(2): p. 137-44.

The invention claimed is:

1. A method of modulating nuclear receptor subfamily 2 group F member 6 (NR2F6) activity by exposure of NR2F6 to an effective amount of a compound capable of having a binding interaction with the ligand binding domain of NR2F6 to modulate NR2F6 activity, wherein said compound is selected from the group consisting of formylindolo (3,2-B) carbazole, 4-hydroxyphenylretinamide, 3,5 -Diiodo-L-tyrosine, Rifampicin, and N-[3-(diethylsulfamoyl)phenyl]-2-(3-pyrrolidin-1-ylsulfonylanilino)acetamide (compound Z30972366), wherein said modulation comprises the augmentation of NR2F6 activity that leads to decreased activity of at least one component of the NR2F6-dependent signaling pathway.

2. The method of claim 1, wherein said decreased activity of at least one component of the NR2F6-dependent signaling pathway comprises decreased activity of NF-AT and AP-1.

3. The method of claim 1, wherein said augmentation of NR2F6 activity leads to suppression of an immune response.

4. The method of claim 3, wherein said exposure of NR2F6 to said compound is performed in vivo in a patient in need of modulation of NR2F6 modulation, wherein said exposure comprises administering a therapeutically effective amount of said compound to said patient and said augmentation of NR2F6 activity leads to suppression of an immune response in said patient.

5. The method of claim 4, comprising treatment of a disease related to an augmented immune response.

6. The method of claim 5, wherein the disease is an autoimmune disease.

7. A method of modulating nuclear receptor subfamily 2 group F member 6 (NR2F6) activity by exposure of NR2F6 to an effective amount of a compound capable of having a binding interaction with the ligand binding domain of NR2F6 activity, wherein said compound is selected from the group consisting of: formylindolo (3,2-B) carbazole, 4-hydroxphenylretinamide, 3,5-Diiodo-L-tyrosine, Rifampcicin, and N-[3-(diethylsulfamoyl)phenyl]-2-(3-pyrrolidin-1-ylsulfonylanilino)acetamide (compound Z30972366), wherein said modulation comprises the inhibition of NR2F6 activity and least to augmentation of an immune response.

8. The method of claim 7, wherein said exposure of NR2F6 to said compound is performed in vivo in a patient in need of modulation of NR2F6 modulation, wherein said exposure comprises administering a therapeutically effective amount of said compound to said patient and said inhibition of NR2F6 activity leads to augmentation of an immune response in said patient.

9. The method of claim 8, wherein the patient is suffering from cancer.

* * * * *

SEQUENCE LISTING

```
<160> NUMBER OF SEQ ID NOS: 2

<210> SEQ ID NO 1
<211> LENGTH: 1804
<212> TYPE: DNA
<213> ORGANISM: Homo sapiens

<400> SEQUENCE: 1
gtgcagcccg tgcccccgc gcgccggggc cgaatgcgcg ccgcgtaggg tccccgggc      60 cgagagggt gcccggaggg aagagcgcgg tggggcgcc ccggccccgc tgccctgggg     120
ctatggccat ggtgaccggc ggctggggcg gccccggcgg cgacacgaac ggcgtggaca    180
aggcgggcgg ctacccgcgc gcggccgagg acgactcggc ctcgcccccc ggtgccgcca    240
gcgacgccga gccgggcgac gaggagcggc cggggctgca ggtggactgc gtggtgtgcg    300
gggacaagtc gagcggcaag cattacggtg tcttcacctg cgagggctgc aagagctttt    360
tcaagcgaag catccgccgc aacctcagct acacctgccg gtccaaccgt gactgccaga    420
tcgaccagca ccaccggaac cagtgccagt actgccgtct caagaagtgc ttccgggtgg    480
gcatgaggaa ggaggcggtg cagcgcggcc gcatcccgca ctcgctgcct ggtgccgtgg    540
ccgcctcctc gggcagcccc ccgggctcgg cgctggcggc agtggcgagc ggcggagacc    600
tcttcccggg gcagccggtg tccgaactga tcgcgcagct gctgcgcgct gagccctacc    660
ctgcggcggc cggacgcttc ggcgcagggg gcggcgcggc gggcgcggtg ctgggcatcg    720
acaacgtgtg cgagctggcg gcgcggctgc tcttcagcac cgtggagtgg gcgcgccacg    780
cgcccttctt ccccgagctg ccggtggccg accaggtggc gctgctgcgc ctgagctgga    840
gcgagctctt cgtgctgaac gcggcgcagg cggcgctgcc cctgcacacg gcgccgctac    900
tggccgccgc cggcctccac gccgcgccta gccgccgcga gcgcgccgtg ctttcatgg    960 accaggtgcg cgccttccag gaggaggtgg acaagctggg ccgcctgcag gtcgactcgg   1020
ccgagtatgc ctgcctcaag gccatcgcgc tcttcacgcc cgacgcctgt ggcctctcag   1080
acccggccca cgttgagagc ctgcaggaga aggcgcaggt ggccctcacc gagtatgtgc   1140
```

-continued

```
gggcgcagta cccgtcccag ccccagcgct tcgggcgcct gctgctgcgg ctccccgccc    1200
tgcgcgcggt ccctgcctcc ctcatctccc agctgttctt catgcgcctg gtggggaaga    1260
cgcccattga cactgatc agagacatgc tgctgtcggg gagtaccttc aactggccct     1320
acggctcggg ccagtgacca tgacggggcc acgtgtgctg tggccaggcc tgcagacaga    1380
cctcaaggga cagggaatgc tgaggcctcg aggggcctcc cggggcccag gactctggct    1440
tctctcctca gacttctatt ttttaaagac tgtgaaatgt ttgtctttc tgtttttaa      1500
atgatcatga aaccaaaaag agactgatca tccaggcctc agcctcatcc tccccaggac    1560
ccctgtccag gatggagggt ccaatcctag gacagccttg ttcctcagca ccctagcat     1620
gaacttgtgg gatggtgggg ttggcttccc tggcatgatg gacaaaggcc tggcgtcggc    1680
cagaggggct gctccagtgg gcaggggtag ctagcgtgtg ccaggcagat cctctggaca    1740
cgtaacctat gtcagacact acatgatgac tcaaggccaa taataaagac atttcctacc    1800
tgca                                                                 1804
```

<210> SEQ ID NO 2
<211> LENGTH: 404
<212> TYPE: PRT
<213> ORGANISM: Homo sapiens

<400> SEQUENCE: 2

```
Met Ala Met Val Thr Gly Gly Trp Gly Pro Gly Gly Asp Thr Asn
1               5                   10                  15
Gly Val Asp Lys Ala Gly Gly Tyr Pro Arg Ala Ala Glu Asp Ser
                20                  25                  30
Ala Ser Pro Pro Gly Ala Ala Ser Asp Ala Glu Pro Gly Asp Glu Glu
            35                  40                  45
Arg Pro Gly Leu Gln Val Asp Cys Val Val Cys Gly Asp Lys Ser Ser
        50                  55                  60
Gly Lys His Tyr Gly Val Phe Thr Cys Glu Gly Cys Lys Ser Phe Phe
65                  70                  75                  80
Lys Arg Ser Ile Arg Arg Asn Leu Ser Tyr Thr Cys Arg Ser Asn Arg
                85                  90                  95
Asp Cys Gln Ile Asp Gln His His Arg Asn Gln Cys Gln Tyr Cys Arg
            100                 105                 110
Leu Lys Lys Cys Phe Arg Val Gly Met Arg Lys Glu Ala Val Gln Arg
        115                 120                 125
Gly Arg Ile Pro His Ser Leu Pro Gly Ala Val Ala Ala Ser Ser Gly
    130                 135                 140
Ser Pro Pro Gly Ser Ala Leu Ala Ala Val Ala Ser Gly Gly Asp Leu
145                 150                 155                 160
Phe Pro Gly Gln Pro Val Ser Glu Leu Ile Ala Gln Leu Leu Arg Ala
                165                 170                 175
Glu Pro Tyr Pro Ala Ala Ala Gly Arg Phe Gly Ala Gly Gly Ala
            180                 185                 190
Ala Gly Ala Val Leu Gly Ile Asp Asn Val Cys Glu Leu Ala Ala Arg
        195                 200                 205
Leu Leu Phe Ser Thr Val Glu Trp Ala Arg His Ala Pro Phe Phe Pro
    210                 215                 220
Glu Leu Pro Val Ala Asp Gln Val Ala Leu Leu Arg Leu Ser Trp Ser
225                 230                 235                 240
Glu Leu Phe Val Leu Asn Ala Ala Gln Ala Ala Leu Pro Leu His Thr
                245                 250                 255
```

```
Ala Pro Leu Leu Ala Ala Ala Gly Leu His Ala Ala Pro Met Ala Ala
        260             265             270

Glu Arg Ala Val Ala Phe Met Asp Gln Val Arg Ala Phe Gln Glu Gln
    275             280             285

Val Asp Lys Leu Gly Arg Leu Gln Val Asp Ser Ala Glu Tyr Gly Cys
    290             295             300

Leu Lys Ala Ile Ala Leu Phe Thr Pro Asp Ala Cys Gly Leu Ser Asp
305             310             315             320

Pro Ala His Val Glu Ser Leu Gln Glu Lys Ala Gln Val Ala Leu Thr
                325             330             335

Glu Tyr Val Arg Ala Gln Tyr Pro Ser Gln Pro Gln Arg Phe Gly Arg
            340             345             350

Leu Leu Leu Arg Leu Pro Ala Leu Arg Ala Val Pro Ala Ser Leu Ile
        355             360             365

Ser Gln Leu Phe Phe Met Arg Leu Val Gly Lys Thr Pro Ile Glu Thr
    370             375             380

Leu Ile Arg Asp Met Leu Leu Ser Gly Ser Thr Phe Asn Trp Pro Tyr
385             390             395             400

Gly Ser Gly Gln
```